(12) United States Patent
Hashimoto et al.

(10) Patent No.: US 10,393,757 B2
(45) Date of Patent: Aug. 27, 2019

(54) DIAGNOSTIC DRUG AND DIAGNOSTIC METHOD FOR ALZHEIMER'S DISEASE

(75) Inventors: Masakazu Hashimoto, Suita (JP); Hiroyuki Nakagawa, Osaka (JP); Mikio Aoki, Osaka (JP); Lars O. Tjernberg, Huddinge (SE); Bengt Winblad, Huddinge (SE)

(73) Assignee: DAINIPPON SUMITOMO PHARMA CO., LTD., Osaka (JP)

( * ) Notice: Subject to any disclaimer, the term of this patent is extended or adjusted under 35 U.S.C. 154(b) by 196 days.

(21) Appl. No.: 13/997,854

(22) PCT Filed: Dec. 28, 2011

(86) PCT No.: PCT/JP2011/080517
§ 371 (c)(1),
(2), (4) Date: Jun. 25, 2013

(87) PCT Pub. No.: WO2012/091138
PCT Pub. Date: Jul. 5, 2012

(65) Prior Publication Data
US 2013/0280732 A1    Oct. 24, 2013

(30) Foreign Application Priority Data
Dec. 28, 2010   (JP) ................. 2010-293891

(51) Int. Cl.
G01N 33/53    (2006.01)
G01N 33/566   (2006.01)
A01N 37/18    (2006.01)
G01N 33/68    (2006.01)
C07K 16/18    (2006.01)

(52) U.S. Cl.
CPC ......... G01N 33/6896 (2013.01); C07K 16/18 (2013.01); *G01N 2800/2821* (2013.01)

(58) Field of Classification Search
None
See application file for complete search history.

(56) References Cited

U.S. PATENT DOCUMENTS 7,368,531 B2 * 5/2008 Rosen ............... C07K 14/47
                                                 435/320.1
2010/0113590 A1 5/2010 Hiruma et al.

FOREIGN PATENT DOCUMENTS

| CN | 101594860 A | 12/2009 |
| JP | 2008-545424 A | 12/2008 |
| WO | WO 2001/077137 A1 | 10/2001 |
| WO | WO 2002/018435 A1 | 3/2002 |
| WO | WO 2003/016493 A2 | 2/2003 |
| WO | WO 2006/128902 A1 | 12/2006 |
| WO | WO 2006/128906 A1 | 12/2006 |
| WO | WO 2008/090717 A1 | 7/2008 |
| WO | WO 2009/048747 A2 | 4/2009 |
| WO | WO 2010/088633 A2 | 8/2010 |
| WO | WO 2010/140694 A1 | 12/2010 |

OTHER PUBLICATIONS

Buntup et al., *Neurochemical Research*, 33(2): 248-256 (2008).
Dahlin et al., *The Journal of Pharmacology and Experimental Therapeutics*, 329(2): 558-570 (2009).
MacKenzie et al., *Flugers Arch.—European Journal of Physiology*, 447(5): 784-795 (2004).
Melone et al., *Cerebral Cortex*, 14(5): 562-574 (2004).
Pontèn et al., *Journal of Internal Medicine*, 270(5): 428-446 (2011).
Sleat et al., *Proteomics*, 5(6): 1520-1532 (2005).
European Patent Office, Supplementary European Search Report in European Patent Application No. 11853134.2 (dated Apr. 2, 2015).
Celestino-Soper et al., *Human Molecular Genetics*, 20(22): 4360-4370 (2011).
Corder et al., *Experimental Gerontology*, 35: 851-864 (2000).
Corder et al., *Science*, New Series, 261(5123): 921-923 (1993).
Jamieson et al., *Neuroscience Letters*, 374: 124-128 (2005).
Laterza et al., *Clinical Chemistry*, 52(9): 1713-1721 (2006).
Nakamura et al., *Molecular Neurodegeneration*, 4(35): 11 pages (Aug. 20, 2009) [doi:10.1186/1750-1326-4-35].
Sundberg et al., *J. Mol. Neurosci.*, 35: 179-193 (2008).
Zheng et al., *FASEB Journal*, 23(12): 4207-4217 (2009).
Japanese Patent Office, International Search Report in International Application No. PCT/JP2011/080517 (dated Feb. 21, 2012).
Japanese Patent Office, International Preliminary Report on Patentability in International Application No. PCT/JP2011/080517 (dated Jul. 10, 2013).
Wu et al., *Molecular & Cellular Proteomics*, 9(6): 1100-1117 and supplementary table (Jun. 2010).
Geldmacher, *Prim. Care Companion J. Clin. Psychiatry*, 9(2): 113-121 (2007).

(Continued)

*Primary Examiner* — Olga N Chernyshev
(74) *Attorney, Agent, or Firm* — Leydig Voit and Mayer, Ltd.

(57) ABSTRACT

The present invention provides an agent for determining Alzheimer's disease, comprising an anti-S38AA antibody, a method of determining Alzheimer's disease in a test animal, comprising detecting an S38AA fragment in a sample collected from said animal, and a method of screening for a substance that treats or prevents Alzheimer's disease, comprising contacting a test substance with a cell permitting measurement of production of a S38AA fragment, measuring the production amount of the S38AA fragment in the cell, and comparing the production amount with that of the S38AA fragment in a control cell free of contact with the test substance, and selecting a test substance that down-regulates the production amount of the S38AA fragment as a substance capable of treating or preventing Alzheimer's disease, based on the comparison results.

2 Claims, 5 Drawing Sheets
Specification includes a Sequence Listing.

(56) References Cited

OTHER PUBLICATIONS

National Center for Biotechnology Information, "Putative sodium-coupled neutral amino acid transporter 10 isoform a [*Homo Sapiens*]," NCBI Reference Sequence: NP_001033073.1 (Dec. 26, 2010) [obtained at: https://www.ncbi.nlm.nih.gov/protein/83921602?sat=14&satkey=5307359 on Sep. 24, 2017)].

Uniprot Consortium, "Putative sodium-coupled neutral amino acid transporter 10 (SLC38A10 Gene and S38AA Protein)," Identification No. Q9HBR0 (Entry Version 110 dated Feb. 13, 2019—Sequence Version 2 dated Feb. 26, 2008) [obtained at https://www.uniprot.org/uniprot/Q9HBR0].

* cited by examiner

Fig. 3

```
              10         20         30         40         50         60
          mtaaaasnwg litnivnsiv gvsvltmpfc fkqcgivlga llvfcswmt hqscmflvks
              70         80         90        100        110        120
          aslskrrtya glafhaygka gkmlvetsmi glmlgtciaf yvvlgdlgsn ffarlfgfqv
             130        140        150        160        170        180
          ggtfrmfllf avslcivlpl slqrnmmasi qsfsamallf ytvfmfvivl sslkhglfsg
             190        200        210        220        230        240
          qwlrrvsyvr wegvfrcipi fgmsfacqsq vlptydslde psvktmssif asslnvvttf
             250        260        270        280        290        300
          yvmvgffgyv sfteatagnv lmhfpsnlvt emlrvgfmms vavgfpmmil pcrqalstll
             310        320        330        340        350        360
          ceqqqkdgtf aaggympplr fkaltlsvvf gtmvggilip nvetilgltg atmgslicfi
             370        380        390        400        410        420
          cpaliykkih knalssqvvl wvglgvlvvs tvttlsvsee vpedlaeeap ggrlgeaegl
             430        440        450        460        470        480
          mkveaarlsa qdpvvavaed grekpklpke reeleqaqik gpvdvpgred gkeapeeaql
             490        500        510        520        530        540
          drpgqglavp vgeahrhepp vphdkvvvde gqdrevpeen kppsrhaggk apgvqgqmap
             550        560        570        580        590        600
          plpdserekq epeqgevgkr pgqaqaleea gdlpedpqkv peadgqpavq pakedlgpgd
             610        620        630        640        650        660
          rglhprpqav lseqqnglav gggekakggp ppgnaagdtg qpaedsdhgg kpplpaekpa
             670        680        690        700        710        720
          pgpglppepr eqrdveragg nqaasqleea graemldhav llqvikeqqv qqkrlldqqe
             730        740        750        760        770        780
          kllavieeqh keihqqrqed eedkprqvev hqepgaavpr gqeapegkar etvenlpplp
             790        800        810        820        830        840
          ldpvlrapgg rpapsqdlnq rslehsegpv grdpagppdg gpdtepraaq aklrdgqkda
             850        860        870        880        890        900
          apraagtvke lpkgpeqvpv pdpareaggp eerlaeefpg qsqdvtggsq drkkpgkeva
             910        920        930        940        950        960
          atgtsilkea nwlvagpgae tgdprmkpkq vsrdlglaad lpggaegaaa qpqavlrqpe
             970        980        990       1000       1010       1020
          lrvisdgeqg gqqghrldhg ghlemrkarg gdhvpvsheq prggedaavq eprqrpepel
            1030       1040       1050       1060       1070       1080
          glkravpggq rpdnakpnrd lklqagsdlr rrrrdlgpha egqlaprdgv iiglnplpdv
            1090       1100       1110
          qvndlrgald aqlrqaagga lqvvhsrqlr qapgppees
```

DIAGNOSTIC DRUG AND DIAGNOSTIC METHOD FOR ALZHEIMER'S DISEASE

CROSS-REFERENCE TO RELATED APPLICATIONS

This patent application is the U.S. national phase of International Patent Application No. PCT/JP2011/080517, filed Dec. 28, 2011, which claims the benefit of Japanese Patent Application No. 2010-293891, filed on Dec. 28, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 30,374 bytes ASCII (Text) file named "713766SequenceListing.txt," created Jun. 24, 2013.

TECHNICAL FIELD

The present invention relates to an agent for determining Alzheimer's disease, a method of determining Alzheimer's disease, and a method of screening for a substance for the treatment or prevention of Alzheimer's disease.

BACKGROUND ART

Alzheimer's disease is a progressive dementia that starts with decrease of short term memory and mild learning disability, develops higher brain dysfunction, particularly visuospatial agnosia, ideational apraxia, constructive apraxia and the like, and finally reaches movement disorder and so-called personality destruction, for which a method of radical treatment has not been found to date. There are predicted to be 2.4 million patients with Alzheimer's disease in the world in 2040, and the importance of a radical treatment method therefor or an early diagnosis thereof is increasing. The progression thereof is different from angiopathic dementia often found in Japan and is considered to continue over several years to ten years or more. In the case of a familial Alzheimer's disease caused by abnormal gene mutation, which is one of the Alzheimer's diseases, the condition of many of the patients rapidly worsens in several years, and the disease is characterized by an early onset since the age at onset is in their 30's-40's. Age, family history, genotype, hypertension, diabetes, smoking and the like are known as the risk factors of Alzheimer's disease other than the gene mutation, of which the relation with APOE genotype is clear. In particular, ApoE4 allele has already been reported as a risk factor of Alzheimer's disease (non-patent document 1).

As pathological changes characteristic in Alzheimer's disease, extracellular accumulation of amyloid plaque containing amyloid beta as a main constituent component, and accumulation of highly phosphorylated tau protein in nerve cells are widely known to occur. As for spatial and temporal pathological changes in brain, since accumulation of phosphorylated tau in the pyramidal cells in the hippocampus, particularly the region called CA1, is already observed in patients with early-onset Alzheimer's disease, the pyramidal cells in this region are considered to be spatially and temporally exposed to the strong influence of Alzheimer's disease in early stages, namely show fragility (non-patent document 2). On the other hand, since the movement disorder emerges almost at the final stage of Alzheimer's disease as mentioned above, the purkinje cell in the cerebellum is considered to be most resistant to Alzheimer's disease.

The incidence rate of Alzheimer's disease is considered to rapidly increase after 75 years old, and early detection and the start of an early treatment are important for suppressing the pathological progression by a symptomatic drug therapy.

Due to the absence of a radical cure for Alzheimer's disease at present, a diagnostic marker for early detection of Alzheimer's disease is energetically searched for, and the measurement of amyloid beta (Aβ40, Aβ42) and phosphorylated tau protein in blood or cerebrospinal fluid is considered to be the most promising. However, it is still difficult to clearly find acquisition of Alzheimer's disease in the future, that is, potential patients with Alzheimer's disease, even when these markers are used alone or in combination (for example, ratio of Aβ40 and Aβ42).

DOCUMENT LIST

Non-Patent Documents non-patent document 1: Science. (1993) 261:921-3
non-patent document 2: Exp Gerontol. (2000) 35:851-64

SUMMARY OF THE INVENTION

Problems to be Solved by the Invention

The problem of the present invention is to provide an agent for determining Alzheimer's disease, a method of determining Alzheimer's disease, and a method of screening for a substance for the treatment or prevention of Alzheimer's disease.

Means of Solving the Problems

The present inventors have conducted intensive studies and found that the amount of S38AA fragment increases in the cerebrospinal fluid and plasma of patients with Alzheimer's disease as compared to normal person, and this S38AA fragment is a polypeptide containing the extra-membranous domain of S38AA isoform 1.

Furthermore, the present inventors have measured the amount of the S38AA fragment in the cerebrospinal fluid of non-Alzheimer's disease (normal person), and patients with suspected Alzheimer's disease (potential Alzheimer's disease) and severe Alzheimer's disease, and found that the amount of the S38AA fragment increases with the worsening pathology (progression) of Alzheimer's disease and, since this pathology-dependent increase in the amount of the S38AA fragment in Alzheimer's disease shows a positive correlation with ApoE4 carrier and a negative correlation with ApoE2 carrier, the S38AA fragment has high reliability as an index for the determination of Alzheimer's disease.

Based on these findings, the present inventors have been convinced that an anti-S38AA antibody is useful as a determining agent for Alzheimer's disease and Alzheimer's disease can be detected by measuring the S38AA fragment, which resulted in the completion of the present invention.

Accordingly, the present invention relates to the following.

[1] An agent for determining Alzheimer's disease, comprising an anti-S38AA antibody.

[2] The determining agent of [1], wherein the anti-S38AA antibody is an antibody recognizing the S38AA extra-membranous domain.

[3] The determining agent of [2], wherein the S38AA extra-membranous domain is an extra-membranous domain of S38AA isoform 1.

[4] A kit for determining Alzheimer's disease, comprising the detecting agent of any of [1]-[3].

[5] A method of determining Alzheimer's disease in a test animal, comprising detecting an S38AA fragment in a sample collected from said animal.

[6] The method of [5], wherein the test animal is a human.

[7] The method of [5] or [6], wherein the S38AA fragment is a fragment derived from S38AA isoform 1.

[8] The method of [5] or [6], wherein the S38AA fragment is a polypeptide comprising an amino acid sequence shown by SEQ ID NO: 3.

[9] The method of any of [5]-[8], wherein the sample is blood, cerebrospinal fluid or urine.

[10] The method of any of [5]-[8], wherein the sample is cerebrospinal fluid.

[11] The method of any of [5]-[10], further comprising detecting one or more other diagnostic markers for Alzheimer's disease.

[12] A method of searching for a substance capable of treating or preventing Alzheimer's disease, comprising the following steps:
(1) contacting a test substance with a cell permitting measurement of production of a S38AA fragment;
(2) measuring the production amount of the S38AA fragment in the cell contacted with the test substance, and comparing the production amount with that of the S38AA fragment in a control cell free of contact with the test substance; and
(3) selecting a test substance that down-regulates the production amount of the S38AA fragment as a substance capable of treating or preventing Alzheimer's disease, based on the comparison results of the above-mentioned (2).

Effect of the Invention

According to the present invention, an agent for determining Alzheimer's disease and a method of determining Alzheimer's disease can be provided.

In addition, according to the screening method of the present invention, an agent capable of treating or preventing Alzheimer's disease can be provided.

BRIEF DESCRIPTION OF THE DRAWINGS

FIG. 3 shows a predicted extra-membrane region of the amino acid sequence of S38AA isoform 1 in the box. The immunoprecipitated S38AA fragment was analyzed by shotgun proteome, and the identified peptide fragment sequence and the position thereof are underlined. The amino acid sequence depicted in FIG. 3 corresponds to SEQ ID NO: 2.

DESCRIPTION OF EMBODIMENTS

Figure 1:
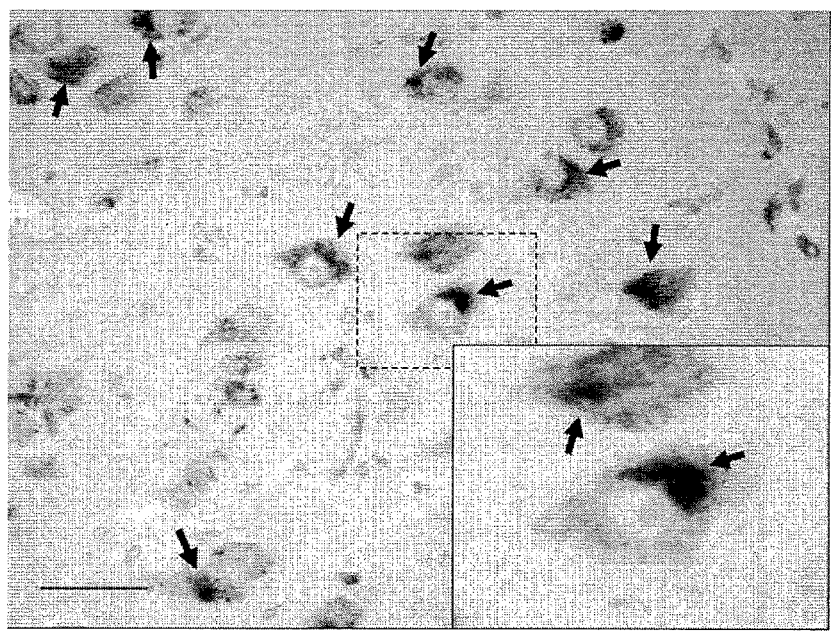
FIG. 1 shows an immunostaining image of a representative hippocampus CA1 region of a normal example. The intensely-stained parts (arrows) in the nerve cell of FIG. 1 show strong expression of S38AA. The lower right panel is an enlarged view of the part enclosed with a broken line. The scale bar shows 20 µm.

Accordingly, the present invention relates to the following.

1. Agent of the Present Invention for Determining Alzheimer's Disease

The present inventors have found that (1) the amount of S38AA fragment increases in the cerebrospinal fluid and plasma of patients with Alzheimer's disease as compared to normal person, (2) the amount of the S38AA fragment is found to increase even in patients with suspected Alzheimer's disease more than in normal person, and the amount of the S38AA fragment increases with the worsening pathology (progression) of Alzheimer's disease, and (3) since this pathology-dependent increase in the amount of the S38AA fragment in Alzheimer's disease shows a positive correlation with ApoE4 carrier and a negative correlation with ApoE2 carrier, the S38AA fragment has high reliability as an index for the determination of Alzheimer's disease.

Accordingly, the present invention provides an agent for determining Alzheimer's disease, comprising an anti-S38AA antibody.

The determining agent of the present invention can determine not only whether a person is affected with Alzheimer's disease but also whether a person is suspected of being affected with Alzheimer's disease, that is, whether the person has a high possibility of being affected with the disease in the near future, though the person is not yet suffering from the disease.

Therefore, the "determination" of Alzheimer's disease in the present invention is used to mean not only determination of whether a person is already affected with Alzheimer's disease, but encompass judgment of whether a person has a high possibility of being affected in the near future, though the person is not yet suffering from the disease.

In the present specification, "suspected Alzheimer's disease" refers to a condition associated with a high possibility of being affected (definitely diagnosed) in the future, though a definite diagnosis of Alzheimer's disease has not been made. Specific examples thereof include the condition to be classified into mild or moderate level by the severity classification in diagnosis according to amyloid imaging, MRI, CT, SPET or clinical symptom, the state of mild cognitive impairment and the like.

As S38AA, for example, amino acid sequences such as human S38AA isoform 1 (UniProtKB/Swiss-Prot number: Q9HBR0-1, SEQ ID NO: 2), rat S38AA isoform 1 (NCBI Reference Sequence number: XP_002727892.1), mouse S38AA isoform 1 (NCBI Reference Sequence number: NP_077211.4), human S38AA isoform 2 (UniProtKB/Swiss-Prot number: Q9HBR0-2) and the like are known.

In addition, as the sequence of a nucleic acid encoding S38AA (hereinafter to be referred to as "S38AA gene"), for example, human S38AA isoform 1 cDNA sequence (NCBI Reference Sequence number: NM_001037984.1, SEQ ID NO: 1) is known.

S38AA is predicted to be a ten-transmembrane protein according to UniProtKB/Swiss-Prot database, and the amino acid sequence from the 399th inclusive (to the 1119th in isoform 1, and to the 780th in isoform 2) is assumed to be the extra-membrane region.

"S38AA" in the present specification encompasses not only "protein" or "(poly) peptide" shown by these known sequences, but also, for example, equivalents thereof (homologs and splice variants), variants, derivatives, mature forms, amino acid-modified forms and the like as long as they have biological functions equivalent to those of a particular amino acid sequence showing human S38AA isoform 1 (SEQ ID NO: 2). Here, examples of the homolog include proteins of other biological species such as mouse, rat and the like, which correspond to human protein. They can be deductively identified from the base sequence of a gene identified by HomoloGene (www.ncbi.nlm.nih.gov/HomoloGene/). Examples of the splice variant include human S38AA isoform 2 (the 689-780th amino acid sequence is different from isoform 1, and the 781-1119th amino acid sequence is deleted). In addition, the variant encompasses naturally-occurring allelic variants (polymorphism), variants not present in nature, and variants having amino acid sequences artificially altered by deleting, substituting, adding or inserting. Examples of the above-mentioned variant include those having at least 70%, preferably 80%, more preferably 95%, further more preferably 97%, identity with a mutation-free protein or (poly) peptide. Examples of the naturally-occurring allelic variant (polymorphism) include, a variant of SEQ ID NO: 2 wherein the 559th Lys is substituted for Arg (ddbSNP: rs35546507) and a variant wherein the 831st Ala is substituted for Gly (dbSNP: rs2725405). In addition, the amino acid-modified form encompasses naturally-occurring amino acid-modified forms and amino acid-modified forms not present in nature, and specifically, amino acid-phosphorylated forms (e.g., phosphorylated form of SEQ ID NO: 2 wherein the 889th Ser is phosphorylated) can be included.

The extra-membranous domain and transmembrane region and the like of a protein can be easily assumed using, for example, prediction data described in UniProtKB/Swiss-Prot database, and a known prediction tool and software such as TMHMM (www.cbs.dtu.dk/services/TMHMM) and the like.

The "S38AA fragment" in the present specification only needs to be a (poly) peptide containing the S38AA extra-membranous domain. The "S38AA extra-membranous domain" here means a peptide region containing the whole or partial extra-membrane region on the C-terminal side of any of the above-mentioned S38AAs, or the whole or partial extra-membrane region on the C-terminal side of S38AA in the cell organelle such as Golgi and the like. In addition, the "S38AA fragment" in the present specification is characterized in that it is recognized by anti-S38AA antibody HPA024631 (Atlas Antibodies; produced using a peptide consisting of the 402-491st amino acid sequence of SEQ ID NO: 2 as immunogen).

Preferably, the S38AA fragment contains the amino acid sequence shown by SEQ ID NO: 3. The amino acid sequence shown by SEQ ID NO: 3 corresponds to the 761-770th partial amino acid sequence of human S38AA isoform 1 (in isoform 2, the amino acid sequence from the 689th inclusive is different due to alternative splicing). Therefore, while the S38AA fragment is preferably a fragment derived from S38AA isoform 1, since the cleavage site of S38AA is predicted, from the apparent molecular weight of S38AA fragment by SDS-PAGE, to be in the amino acid sequence (up to the 688th amino acid of SEQ ID NO: 2) common to the two isoforms, if the cleavage reaction occurs upon recognition of only the amino acid sequence in the cleavage site, a fragment derived from isoform 2 can also be included in the S38AA fragment of the present invention.

While the molecular weight of the S38AA fragment is not limited, it is preferably about 76-about 102 kDa in the apparent molecular weight by SDS-PAGE. Therefore, a fragment cleaved after the 161st amino acid of the amino acid sequence shown by SEQ ID NO: 2 is more preferable (molecular weight (Calculated) of the fragment consisting of the 161-1119th amino acid sequence is about 102 kDa). In addition, from the results of the pull-down assay and shotgun MS analysis mentioned below, the S38AA fragment of the present invention is more preferably a fragment containing the 505-1014th amino acid sequence of the amino acid sequence shown by SEQ ID NO: 2.

The "anti-S38AA antibody" in the present invention is an antibody that recognizes the S38AA extra-membranous domain, with preference given to an antibody that recognizes the extra-membranous domain of S38AA isoform 1. Said extra-membranous domain may be in the amino acid region specific to isoform 1 (in SEQ ID NO: 2, the 689-1119th amino acid region), in the amino acid region common with isoform 2 (the 399-688th amino acid region) or go across the both regions. In addition, the extra-membranous domain may be a continuous partial amino acid sequence in the S38AA extra-membrane region or a conformation formed by two or more separate and subsequent partial amino acid sequences.

The anti-S38AA antibody may also be, for example, polyclonal or monoclonal antibody produced by using a known method, such as commercially available anti-S38AA antibodies (e.g., HPA024631, HPA023161, HPA021374 (each manufactured by Atlas Antibodies)) and the like, or fragments thereof (e.g., Fab, F(ab')$_2$, ScFv, minibody etc.).

As the anti-S38AA antibody to be used in the present invention, a monoclonal antibody and a polyclonal antibody derived from mammals are preferable.

Examples of the monoclonal antibody and polyclonal antibody derived from mammals include those produced in the blood of animal, those produced by hybridomas, and those produced by a host transformed with an expression vector containing an antibody gene by a genetic engineering means, those produced in large amounts in a CHO cell factory by the gene of an optimal antibody screened for from an enormous clone library consisting of 1,000,000,000,000 molecules by phage display, or human antibody directly produced using transgenic mouse that produces human antibody, and the like.

Monoclonal antibody and polyclonal antibody can be produced by a known method to those of ordinary skill in the art.

(1) Production of Monoclonal Antibody

S38AA is administered alone or together with a carrier and a diluent to a site where an antibody can be produced by administration to a mammal. To increase antibody producibility by administration, a complete Freund's adjuvant or incomplete Freund's adjuvant may also be administered. The administration is generally performed once every 2-6 weeks, and about 2-10 times in total. Examples of the mammal to be used include monkey, rabbit, dog, guinea pig, mouse, rat, sheep and goat, with preference given to mouse and rat.

For the production of monoclonal antibody-producing cells, from mammals, for example, mice immunized with an antigen, individuals found to show an antibody titer are selected, the spleen or lymph node is collected 2-5 days after the final immunization, the antibody-producing cells contained therein are fused with myeloma cells, whereby a monoclonal antibody-producing hybridoma can be prepared. The antibody titer in antiserum can be measured by, for example, reacting the below-mentioned labeled S38AA with antiserum, and measuring the activity of a label bound to the antibody. A fusion operation can be performed by a known method, for example, the method of Köhler and Milstein [Nature, 256, 495 (1975)]. As the fusion Stimulant, for example, polyethylene glycol (PEG), Sendai virus and the like can be mentioned, and PEG is preferably used.

As the myeloma cell, for example, NS-1, P3U1, SP2/0 and the like can be mentioned, and P3U1 is preferably used. A preferable ratio of the numbers of the antibody-producing cells (spleen cells) and myeloma cells to be used is about 1:1-20:1, PEG (preferably PEG 1000-PEG 6000) is added at a concentration of about 10-80%, and the cell fusion can be efficiently performed by incubating at about 20-40° C., preferably about 30-37° C., for about 1-10 min.

For screening for a monoclonal antibody-producing hybridoma, various methods can be used. Examples thereof include a method comprising adding a hybridoma culture supernatant to a solid phase (e.g., microplate) adsorbed with an antigen such as a protein and the like directly or together with a carrier, adding an anti-immunoglobulin antibody labeled with a radioactive substance, an enzyme or the like (when the cell used for cell fusion is from a mouse, an anti-mouse immunoglobulin antibody is used) or protein A, and detecting a monoclonal antibody bound to the solid phase, a method comprising adding a hybridoma culture supernatant to a solid phase adsorbed with an anti-immunoglobulin antibody or protein A, adding a protein labeled with a radioactive substance, an enzyme etc., and the like, and detecting a monoclonal antibody bound to the solid phase, and the like.

The monoclonal antibody can be selected by a method known per se or a method analogous thereto, and can be generally selected using a medium for animal cells which is added with HAT (hypoxanthine, aminopterine, thymidine), and the like. As the medium for selection and growth, any medium can be used as long as hybridomas can grow. For example, RPMI 1640 medium containing 1-20%, preferably 10-20%, of fetal bovine serum, GIT medium containing 1-10% of fetal bovine serum (Wako Pure Chemical Industries, Ltd.), a serum-free medium for hybridoma culture (SFM-101, Nissui Pharmaceutical Co., Ltd.) and the like can be used. The culture temperature is generally 20-40° C., preferably about 37° C. The culture time is generally 5 days-3 weeks, preferably 1 week-2 weeks. Culture can be generally performed in 5% carbon dioxide gas. The antibody titer of the hybridoma culture supernatant can be measured in the same manner as in the above-mentioned measurement of the antibody titer of the antiserum.

The monoclonal antibody can be separated and purified according to a separation and purification method of immunoglobulin, in the same manner as in general separation and purification of polyclonal antibody [e.g., salting out method, alcohol precipitation method, isoelectric point precipitation method, electrophoresis, adsorption and desorption method by ion exchanger (e.g., DEAE), ultracentrifugation method, gel filtration method, specific purification method including collecting only an antibody by an active adsorbent such as antigen-bound solid phase, protein A, protein G or the like, and dissociating the bond to give the antibody].

(2) Production of Polyclonal Antibody

Polyclonal antibody to S38AA can be produced by a method known per se or a method analogous thereto. For example, a polyclonal antibody can be produced by producing a complex of an immunizing antigen (antigen such as protein and the like) and a carrier protein, immunizing a mammal in the same manner as in the above-mentioned production method of the monoclonal antibody or chicken, collecting a substance containing an antibody to S38AA from the immunized animal, and separating and purifying the antibody.

As for the complex of an immunizing antigen and a carrier protein to be used for immunizing a mammal or chicken, the kind of the carrier protein and the mixing ratio of the carrier and hapten may be any and any ratio as long as the antibody can be efficiently produced against hapten used for immunization by crosslinking with the carrier. For example, a method including coupling bovine serum albumin, bovine thyroglobulin, keyhole limpet hemocyanin and the like at a weight ratio of about 0.1-20, preferably about 1-5, to hapten of 1 is used.

While various condensing agents can be used for coupling hapten with a carrier, an activated ester reagent containing glutaraldehyde, carbodiimide, maleimide activated ester, a thiol group and a dithiopyridyl group, and the like can be used.

The condensation product is administered to a mammal or chicken alone or together with a carrier and a diluent to a site where an antibody can be produced. To increase antibody producibility by administration, a complete Freund's adjuvant or incomplete Freund's adjuvant may also be administered. The administration is generally performed once every 2-6 weeks, and about 3-10 times in total.

The polyclonal antibody can be collected from the blood, ascites, mother's milk and the like of the mammal immunized by the above-mentioned method, preferably from the blood, and in the case of chicken, it can be collected from the blood and egg-yolk.

The titer of the polyclonal antibody in the antiserum can be measured in the same manner as in the above-mentioned measurement of the antibody titer of the antiserum. The polyclonal antibody can be separated and purified according to a separation and purification method of immunoglobulin, in the same manner as in the above-mentioned separation and purification of monoclonal antibody.

2. Kit for Determining Alzheimer's Disease

The present invention provides a kit for determining Alzheimer's disease. The kit of the present invention contains a reagent for measuring the amount of the S38AA fragment. By measuring the amount of the S38AA fragment using the kit of the present invention, Alzheimer's disease can be determined.

The kit of the present invention specifically contains an anti-S38AA antibody that recognizes S38AA. Examples of the anti-S38AA antibody include the anti-S38AA antibody described in detail in the aforementioned "1. Agent of the present invention for determining Alzheimer's disease". The antibody may be a fluorescence-labeled antibody, enzyme-labeled antibody, streptavidin-labeled antibody, biotin-labeled antibody or radioactive-labeled antibody.

The anti-S38AA antibody is generally contained in the kit of the present invention in the form of an aqueous solution thereof dissolved in water or a suitable buffer (e.g., TE buffer, PBS etc.) at a suitable concentration or a freeze-dried product.

The kit of the present invention may further contain, in its constitution, other components necessary for performing the method, according to the measurement method of S38AA fragment. For example, for measurement by Western blot, the kit of the present invention can further contain a blotting buffer, a labeling reagent, a blotting membrane and the like, a determination reagent, a standard solution and the like. Examples of the "standard solution" here include an aqueous solution obtained by dissolving a purified standard product of the above-mentioned "S38AA fragment" in water or a suitable buffer (e.g., TE buffer, PBS and the like) at a particular concentration.

For measurement by sandwich ELISA, the kit of the present invention can further contain, in addition to the above, an immobilized antibody measurement plate, a washing solution and the like. For measurement by an agglutination method including latex agglutination method, an antibody-coated latex, gelatin or the like can be contained. For measurement by a chemical fluorescence method or a chemical fluorescence electron method, antibody-conjugated magnetic particles and a suitable buffer can be contained. For detection of S38AA by using LC/MS, LC-MS/MS or an immunochromatography method, an antibody-coated column or micro column, and a macro chip can be contained as a part of the detection instrument. Furthermore, in a time-resolved fluorescence measurement method or a fluorescence measurement method similar thereto, a plurality of labeled anti-S38AA antibodies and other necessary components may be contained in the constitution.

3. Method for Determining Alzheimer's Disease

The present inventors have found that (1) the amount of S38AA fragment increases in the cerebrospinal fluid and plasma of patients with Alzheimer's disease as compared to normal person, (2) the amount of the S38AA fragment is found to increase even in patients with mild Alzheimer's disease more than in normal person, and the amount of the S38AA fragment increases with the worsening pathology (progression) of Alzheimer's disease, and (3) since this pathology-dependent increase in the amount of the S38AA fragment in Alzheimer's disease shows a positive correlation with ApoE4 carrier and a negative correlation with ApoE2 carrier, the S38AA fragment has high reliability as an index for the determination of Alzheimer's disease.

Thus, the present invention provides a method for determining Alzheimer's disease comprising detecting an S38AA fragment in a sample collected from a test animal.

The determination method of the present invention can determine not only whether a person is affected with Alzheimer's disease but also whether the person has a high possibility of being affected with the disease in the near future, though the person is not yet suffering from the disease.

The detection method of the present invention contains a step of detecting an S38AA fragment in a test sample collected from a test animal, and a step of determining Alzheimer's disease based on the positive correlation between the amount of the S38AA fragment and Alzheimer's disease.

While the animal that can be a test subject for the determination method of the present invention is not particularly limited as long as it produces S38AA, for example, mammals (e.g., human, monkey, bovine, swine, horse, dog, cat, sheep, goat, rabbit, hamster, guinea pig, mouse, rat etc.), birds (e.g., chicken etc.) and the like can be mentioned. Preferred is a mammal, and more preferred is a human.

While a biological sample derived from a test animal to be the sample is not particularly limited, for example, blood, serum, plasma, saliva, urine, cerebrospinal fluid and the like can be mentioned. More preferred is plasma or cerebrospinal fluid.

Serum and plasma can be prepared by collecting blood from a test animal according to a conventional method, and separating the liquid component. The cerebrospinal fluid can be collected by a known means such as spinal tap and the like.

An S38AA fragment in a sample can be detected by a known method. It can be detected by subjecting to, for example, Western blot, gel electrophoresis (e.g., SDS-PAGE, two-dimensional gel electrophoresis and the like), various separation and purification methods (e.g., ion exchange chromatography, hydrophobic chromatography, gel filtration chromatography, affinity chromatography, reversed-phase chromatography, isoelectric point chromatography, capillary electrophoresis and the like), ionization method (e.g., electron impact ionization method, field desorption method, secondary ionization method, fast atom bombardment, matrix assisted laser desorption/ionization (MALDI) method, electrospray ionization method and the like), mass spectrometer (e.g., double-focusing mass spectrometer, quadrupol mass spectrometer, time-of-flight mass spectrometer, Fourier-transform mass spectrometer, ion cyclotron mass spectrometer and the like) and the like.

In addition, the S38AA fragment can be detected according to a known immunochemical method (nephelometry, competitive method, immunometric method, chemical fluorescence method, chemical fluorescence electron method, sandwich method etc.). As for these immunochemical methods, reference can be made to, for example, "Radioimmunoassay" edited by Hiroshi Irie (Kodansha, published in 1974), "radioimmunoassay (sequel)" edited by Hiroshi Irie (Kodansha, published in 1979), "Enzyme Immunoassay" edited by Eiji Ishikawa et al. (the 3rd edition, Igaku-Shoin, published in 1987), "Methods in ENZYMOLOGY" Vol. 121 (Immunochemical Techniques (Part I: Hybridoma Technology and Monoclonal Antibodies)) (published by Academic Press) and the like.

Examples of the anti-S38AA antibody capable of specifically detecting S38AA include the anti-S38AA antibody described in detail in "1. Agent of the present invention for determining Alzheimer's disease".

Then, based on the concentration of the detected S38AA fragment, Alzheimer's disease can be detected. As shown in the below-mentioned Example 2, the concentration of the S38AA fragment in the cerebrospinal fluid of patients with Alzheimer's disease and patients with suspected Alzheimer's disease is higher than that of normal person, and the concentration of the S38AA fragment in the plasma is also higher in patients with Alzheimer's disease than in normal person. Based on the positive correlation between the concentration of the S38AA fragment and Alzheimer's disease therefore, a diagnosis of Alzheimer's disease can be made when the concentration of the S38AA fragment in the sample is high.

Furthermore, even for normal persons, an ApoE4 carrier group, which is an Alzheimer's disease sensitive allele (Alzheimer's disease high risk group), shows a high concentration of the S38AA fragment in the cerebrospinal fluid as compared to a homo ApoE3 genotype group. Conversely, an ApoE2 carrier group, which is an Alzheimer's disease resistant allele, shows a low concentration of the S38AA fragment in the cerebrospinal fluid as compared to the homo ApoE3 genotype group. Therefore, a high concentration of the S38AA fragment in the sample can be judged to show a high possibility of being affected Alzheimer's disease in the future.

The determination method of the present invention can determine Alzheimer's disease with higher precision by measuring, in addition to the S38AA fragment, alteration of other diagnostic markers for Alzheimer's disease. Examples of other diagnostic markers for Alzheimer's disease include known markers such as amyloid beta (Aβ40, Aβ42), phosphorylated tau protein and the like. These can be detected according to a conventional well-known detection method.

4. Method for Searching for Substance Capable of Treating or Preventing Alzheimer's Disease The present invention also provides a method for searching for a substance that treats or prevents Alzheimer's disease, which comprises evaluating whether a test substance suppresses production of an S38AA fragment, and a substance obtainable by said method. In the search method of the present invention, a substance that down-regulates the production of an S38AA fragment is selected as a substance that treats or prevents Alzheimer's disease.

The test substance to be subjected to the search method of the present invention may be any known or novel compound. Examples thereof include nucleic acid, carbohydrate, lipid, protein, peptide, organic low-molecular-weight compound, compound library produced using a combinatorial chemistry technique, random peptide library, natural component derived from microorganism, animals and plants, marine organism etc., and the like.

The search method of the present invention comprises the following steps:

(1) contacting a test substance with a cell permitting measurement of production of a S38AA fragment;
(2) measuring the production amount of the S38AA fragment in the cell contacted with the test substance, and comparing the production amount with that of the S38AA fragment in a control cell free of contact with the test substance; and
(3) selecting a test substance that down-regulates the production amount of the S38AA fragment as a substance capable of treating or preventing Alzheimer's disease, based on the comparison results of the above-mentioned (2).

The "cell" to be used for the search method of the present invention means a cell permitting evaluation of the production level of the measurement target, an S38AA fragment. Examples of the cell include a cell capable of naturally producing the S38AA fragment of the measurement target, an S38AA-expressing cell capable of producing an S38AA fragment by stimulation, and a genetically engineered cell to be able to produce an S38AA fragment.

The measurement target, that is, the cell capable of naturally producing an S38AA fragment, is not particularly limited and, as such cell, a primary cultured cell of a mammal (for example, human, mouse etc.), a cell line induced from said primary cultured cell and the like can be used.

S38AA is known to be expressed in U251 cell and SHSY-5Y cell, and is also expressed in BE(2)-C cell and SK-N-MC cell. In addition, a genetically engineered cell overexpressing S38AA or labeled S38AA with FLAG tag etc., and the like can also be produced using a known technique. By culture, S38AA is cleaved from the S38AA expressing cell and the produced S38AA fragment is liberated. When the amount of the produced S38AA fragment is small, the production of the S38AA fragment can be measured by cultivating, as appropriate, under conditions easily causing the cleavage of S38AA.

Examples of the conditions easily causing the cleavage of S38AA include cultivating in a glucose depletion medium or a medium containing a substance known to physiologically stimulate the brain. Specific examples of such substance include cytokines such as TNFα, interferon-γ, interleukin-1, interleukin-6 and the like, amyloid beta or aggregate thereof and the like.

The test substance and the cell permitting measurement of the production of an S38AA fragment are contacted in a culture medium. The culture medium is appropriately selected according to the cell permitting measurement of the production of an S38AA fragment. Examples thereof include minimum essential medium (MEM), Dulbecco's modified Eagle medium (DMEM), containing about 5-20% of fetal bovine serum, and the like. The culture conditions are appropriately determined in the same manner. For example, the pH of the medium is about 6-about 8, the culture temperature is generally about 30-about 40° C., and the culture time is about 0.1-about 72 hr.

The production amount of the S38AA fragment can be measured by measuring the amount of the S38AA fragment liberated in the cell culture supernatant according to the method described in the item of (3. Method for determining Alzheimer's disease).

The production amount can be preferably compared based on the presence or absence of a significant difference. The production amount of an S38AA fragment in the control cell free of contact with the test substance may be measured before or simultaneously with the measurement of the production amount of the S38AA fragment in the cell contacted with the test substance.

Hence, a substance obtained by comparison that down-regulates the production amount of the S38AA fragment, is selected as an agent capable of treating or preventing Alzheimer's disease.

The compound obtained by the search method of the present invention is useful as a candidate substance for the development of a new therapeutic or preventive agent for Alzheimer's disease.

EXAMPLES

The present invention is explained in the following by referring to the Examples, which do not limit the present invention in any manner.

Reference Example 1

Study of S38AA Expression Amount in Brain Tissue

A brain section preserved in the Swedish brain bank (Brain Power), use of which was permitted by the Ethical Committee of the Karolinska Institute, was used. A hippocampus section (5 micrometers thick) was sliced from a brain tissue block fixed with formalin and embedded in paraffin, and adhered to a slide glass. After a deparaffinization and hydrophilic treatment with xylene-alcohol, the antigen was retrieved by heating at 121° C. for 25 min in Diva Decloaker (BIOCARE MEDICAL). After cooling, a non-specific reaction was blocked with 3% goat whole serum diluted with Tris buffered saline (pH 7.6), and thereafter an anti-38AA antibody (catalog number: HPA024631, Atlas Antibodies) diluted 200-fold with Tris buffered saline was incubated overnight with the specimen at 4° C. After washing with Tris buffered saline, the specimen was incubated with a biotinylated goat anti-rabbit IgG antibody diluted 300-fold, at room temperature for 1 hr. Thereafter, for color development, the specimen was treated with Vectastain Elite ABC kit (Vector Laboratories) for 30 min and further with 3-3-diaminobenzidine-4HCl (DAB/$H_2O_2$) for color development. For counter staining, hematoxylin was used.

Figure 2:
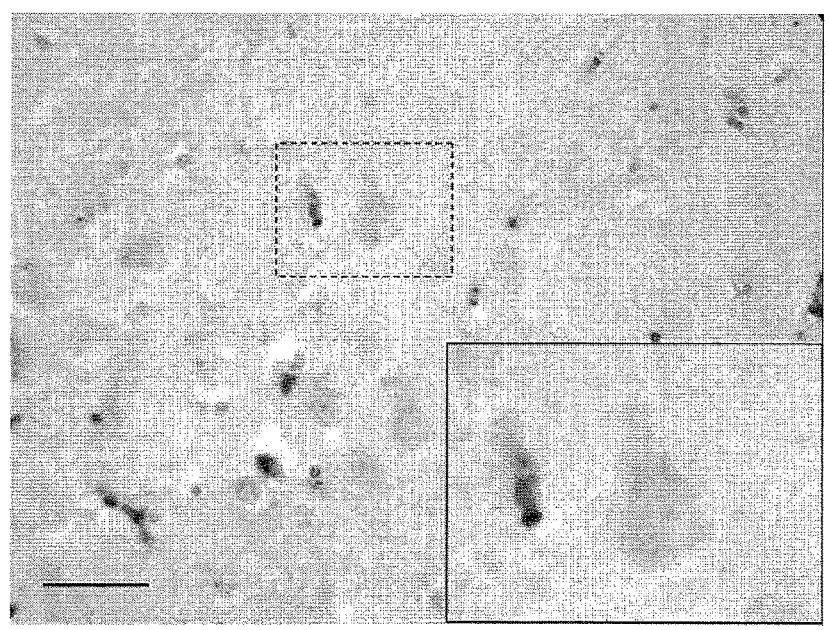
FIG. 2 shows an immunostaining image of a representative hippocampus CA1 region of an example of definite Alzheimer's disease. The lower right panel is an enlarged view of the part enclosed with a broken line. The scale bar shows 20 µm.

FIG. 1 shows an immunostaining image of a representative hippocampus CA1 region of a normal example, and FIG. 2 shows an immunostaining image of a representative hippocampus CA1 region of a case with definite Alzheimer's disease. The length of the bar in the Figure corresponds to 200 μm. As shown with the arrows in FIG. 1, the deeply-stained parts in the cell show strong expression of S38AA. In the case of severe Alzheimer's disease, staining is scarcely found in nerve cells. Since the recognition site of the anti-38AA antibody used is the extra-membranous domain of S38AA isoform 1 and S38AA isoform 2, the results show a decrease in the S38AA extra-membranous domain in the hippocampus CA1 region in a case of Alzheimer's disease with definite diagnosis. From these results, it is clear that the S38AA expression amount drastically decreases in the case of severe Alzheimer's disease.

Reference Example 2

Quantitative Mass Spectrometry of S38AA Protein in Hippocampus CA1 Pyramidal Cell by Heavy Oxygen Labeling Method After obtaining use permission from the Ethical Committee of the Karolinska Institute, a frozen section was prepared from the patients-postmortem brain preserved in the Swedish brain bank (Brain Power), and the hippocampus CA1 pyramidal cells were recovered by a laser capture method according to the method of Aoki et al. already reported (Neuroreport (2008) 19:1085-9).

Hippocampus CA1 pyramidal cells (each 12,000 cells) were separated and collected from a patient with definite Alzheimer's disease and a non-Alzheimer's disease patient. The cells recovered in a tube were lysed with 1 μL of 0.5% RapiGest SF (Waters) solution, and incubated at 95° C. for 90 min. Thereafter, the solvent was removed by a centrifugal vacuum system, 2 μL of 4 mM calcium chloride, 1% RapiGest SF, 360 mM sodium hydrogen carbonate mixed solution and 5 μL of distilled water were further added, and the mixture was subjected to a sonication treatment for 5 min. For limited trypsinolysis of a protein derived from the nerve cell, 3 μL of 0.1 mg/mL trypsin was further added, and the mixture was incubated at 37° C. for 24 hr. Thereafter, a sample (1 μL) was collected and electrophoresed on 4-12% gradient SDS-PAGE gel, subjected to silver staining, and the completion of the limited degradation was confirmed. The limited degradation sample derived from the patient with definite Alzheimer's disease was labeled with heavy oxygen. The detail of the method is as described below.

After limited trypsinolysis, concentrated hydrochloric acid (3 μL) was added to chemically degrade RapiGest SF. The resulting degradation product was precipitated by centrifugation at 13,000 rpm for 10 min, and the supernatant was separated. The obtained supernatant was adsorbed to ZipTipC$_{18}$ (Millipore) column, washed three times with 0.3% formic acid solution, and purified by eluting with 80% acetonitrile/0.3% formic acid solution. The solvent in the purified sample was removed by a centrifugal vacuum system, and the residue was re-dissolved in 0.3 M sodium acetate deuterium solution (pH 5.2, 1.7 μL), 50 mM calcium chloride (1 μL) and heavy oxygen water (47.3 μL). Thereto was added 0.5 mg/mL trypsin (Trypsin Gold, Promega, 1 μL) and the mixture was incubated at 37° C. for 48 hr. To quench the labeling reaction, 5% formic acid solution (8 μL) diluted with heavy oxygen water was added and the mixture was incubated at 95° C. for 90 min. The final sample was preserved at −80° C. While the sample derived from the non-Alzheimer's disease patient was treated in the same manner as the sample derived from the patient with definite Alzheimer's disease, distilled water was used instead of heavy oxygen water. Immediately before conducting mass spectrometry, an equal amount of 20 μL each of the heavy oxygenated sample derived from the patient with definite Alzheimer's disease and the sample derived from the non-Alzheimer's disease patient were mixed, and injected to an analysis column (Zorbax 300SB, 0.1×150 mm, Agilent Technologies Inc.). As the mobile phase for analysis, used were 0.1% acetic acid (mobile phase A) and 0.1% acetic acid-methanol (mobile phase B), wherein a gradient program of increasing the concentration of mobile phase B linearly from 5% to 75% for 90 min, and thereafter maintaining same in 95% mobile phase B for 10 min was used. As mass spectrometer, Thermo Fisher, LTQ-Orbitrap system was used. The mass measurement range was set to 400-2000 m/z. Using the obtained data, the peptide was identified by Mascot software version 2.2 and Swiss-Prot database (release 55), and further, quantitatively analyzed by Xome software (Mitsui Knowledge Industry Co., Ltd.). The analysis parameter on the Mascot software is as follows. The monoisotopic mass was used for the analysis, the peptide mass tolerance was set to 10 ppm and the fragment ion MS/MS tolerance was set to 0.8 Da. As a digestive enzyme, trypsin was specified, and the missed cleavage number was set to 1 at maximum. The analysis target was C-terminal double-label alone, and methionine oxidation was allowed.

According to the above-mentioned proteome analysis, S38AA was successfully identified. Furthermore, the difference in the S38AA expression amount was studied between Alzheimer's disease patients (AD) and non-Alzheimer's disease patients (control) (Table 1). The identified sequence by MASCOT peptide search corresponds to the extra-membranous domain of S38AA isoform 1 (the 761-770th amino acid region of the amino acid sequence shown by SEQ ID NO: 2), and the peptide identification was statistically significant.

The amount of the S38AA extra-membranous domain in the pyramidal cells decreased to 1/20 in Alzheimer's disease patients as compared to non-Alzheimer's disease control. The recognition site of the antibody used in the immunohistological to study was an extra-membranous domain, and since the expression amount also decreased even in that case, the results matched with those of the immunohistological study. That is, it is clear that at least the S38AA extra-membranous domain decreases in the nerve cells of the hippocampus CA1 region in Alzheimer's disease.

TABLE 1

| Alzheimer's disease patient/non-Alzheimer's disease patient expression amount ratio | identified peptide sequence | significance level of identification |
|---|---|---|
| 0.053 | GQEAPEGKAR (SEQ ID NO: 3) | 0.032 |

Example 1

Detection and Molecular Weight Prediction of S38AA Fragment in Cerebrospinal Fluid The cerebrospinal fluids of patients diagnosed with definite Alzheimer's disease (10 cases, pathological score 9-12: pathological score in the Swedish brain bank), suspected Alzheimer's disease (6 cases, pathological score 3-7) and normal (11 cases, pathological score 0-4) were used. The scoring was performed according to the evaluation method of Alafuzoff et al. (Acta Neuropathol (Berl) (1987) 74: 209-225). The pathology determinaion was performed taking into consideration the pathological score and antemortem examination by clinicians. SDS sample was prepared by adding 1 volume of an LDS sample buffer (Invitrogen) relative to 3 volumes of cerebrospinal fluid and heating the mixture at 70° C. for 10 min. Using the prepared sample (10 μL), S38AA was separated on 4-12% gradient SDS-PAGE gel. Thereafter, using Mini Trans-Blot system (Bio-Rad Laboratories), the separated total protein was transferred to PVDF membrane, and applied to the step of antibody staining. Prior to the detection of S38AA with the antibody, the PVDF membrane was blocked from non-specific reactions with 5% skim milk-containing phosphate buffered saline (pH 7.4) at room temperature for 1 hr. The primary antibody (catalog number: HPA024631, Atlas Antibodies) was diluted 1000-fold with phosphate buffered saline and the membrane was incubated with the diluted antibody at 4° C. overnight. Thereafter, the membrane was incubated with 50000-fold diluted HRP-conjugated goat anti-rabbit IgG antibody (GE healthcare) at room temperature for 1 hr, sufficiently washed and treated with SuperSignal (registered trade mark) West Dura (Thermo Fisher Scientific) to allow color development.

Figure 4:
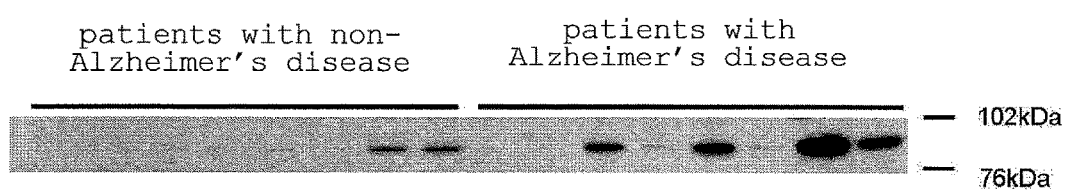
FIG. 4 shows an example of Western blot analysis of S38AA in the cerebrospinal fluid and the results of molecular weight analysis of the detected S38AA fragment.

A signal derived from S38AA fragment in the cerebrospinal fluid could be detected by Western blot, and it was found the intensity thereof tended to increase in Alzheimer's disease (FIG. 4). The detected molecular weight was 76-102 kDa, corresponding to the full-length of S38AA isoform 2. However, isoform 2 is a ten-transmembrane protein having a considerably low possibility of the full-length protein being secreted in the cerebrospinal fluid. Hence, the possibility of partial cleavage and secretion of S38AA was examined.

The amino acid sequence of S38AA isoform 1 was obtained from the registered information of UniProtKB database. The extra-membrane region was predicted using TMHMM software, and the obtained predicted extra-membrane region is shown in a box (FIG. 3). The extra-membrane region consisted of 721 amino acids from the 399th to the 1119th and the molecular weight was calculated to be about 76 kDa. On the other hand, the molecular weight of S38AA in the cerebrospinal fluid was estimated to be about 76-102 kDa by Western blot (FIG. 4), which almost matched with the assumed molecular weight size of the extra-membrane region. From the aspect of the molecular weight, the S38AA detected in the cerebrospinal fluid was suggested to be a (poly) peptide (S38AA fragment) containing the extra-membranous domain of isoform 1.

Example 2

Patient Background, Quantitative Analysis of S38AA Fragment in Cerebrospinal Fluid and Correlation with APOE Allele For quantitative analysis, cerebrospinal fluids of several cases were mixed in advance, and used as the standard cerebrospinal fluid for all analyses. All samples were treated in the same manner, and a standard curve was drawn for each SDS-PAGE gel. Western blot for quantitative analysis of the S38AA fragment was performed in the same manner as in Example 1. The signal intensity derived from S38AA antibody was image analyzed by LAS3000 image analyzer (Fujifilm Corp.) and quantified using MultiGauge V3.0 software (Fujifilm Corp.). Each signal intensity was normalized by the standard curve prepared from the standard cerebrospinal fluid transferred simultaneously onto each membrane.

As for the patients' background, specific patient numbers were accorded in the present test from the aspect of protection of personal information, which did not match with the reference numbers used by the Swedish brain bank. APOE genotype was analyzed according to the standard procedure manual of the Swedish brain bank. The genotype was known for the patients of 27 cases (Table 2) and the analysis was performed using the same.

TABLE 2

| Alzheimer's disease severity classification | patient No. | diagnosis | score | ApoE allele |
|---|---|---|---|---|
| normal | 1 | non-Alzheimer's disease | 01 | 3/3 |
| | 2 | non-Alzheimer's disease | 04 | 2/3 |
| | 3 | non-Alzheimer's disease | 02 | 2/3 |
| | 4 | non-Alzheimer's disease | 00 | 3/4 |
| | 5 | non-Alzheimer's disease | 00 | 3/3 |
| | 6 | non-Alzheimer's disease | 01 | 3/3 |
| | 7 | non-Alzheimer's disease | 04 | 3/4 |
| | 8 | non-Alzheimer's disease | 02 | 3/3 |
| | 9 | non-Alzheimer's disease | 00 | 2/3 |
| | 10 | non-Alzheimer's disease | 00 | 2/3 |
| | 11 | non-Alzheimer's disease | 00 | 3/3 |
| mild or moderate | 12 | suspected Alzheimer's disease | 06 | 3/4 |
| | 13 | suspected Alzheimer's disease | 03 | 3/3 |
| | 14 | suspected Alzheimer's disease | 07 | 3/4 |

TABLE 2-continued

| Alzheimer's disease severity classification | patient No. | diagnosis | score | ApoE allele |
|---|---|---|---|---|
| | 15 | suspected Alzheimer's disease | 07 | 3/4 |
| | 16 | suspected Alzheimer's disease | 07 | 3/3 |
| | 17 | suspected Alzheimer's disease | N.D. | 3/3 |
| severe | 18 | definite Alzheimer's disease | 10 | 3/3 |
| | 19 | definite Alzheimer's disease | 10 | 3/4 |
| | 20 | definite Alzheimer's disease | 12 | 3/4 |
| | 21 | definite Alzheimer's disease | 11 | 3/4 |
| | 22 | definite Alzheimer's disease | 10 | 3/4 |
| | 23 | definite Alzheimer's disease | 11 | 4/4 |
| | 24 | definite Alzheimer's disease | 09 | 4/4 |
| | 25 | definite Alzheimer's disease | 09 | 3/4 |
| | 26 | definite Alzheimer's disease | 10 | 3/4 |
| | 27 | definite Alzheimer's disease | N.D. | 4/4 |

N.D.: not determined
score: evaluation method of Alafuzoff et al. (Acta Neuropathol (1987) 74: 209-225).

Figure 5:
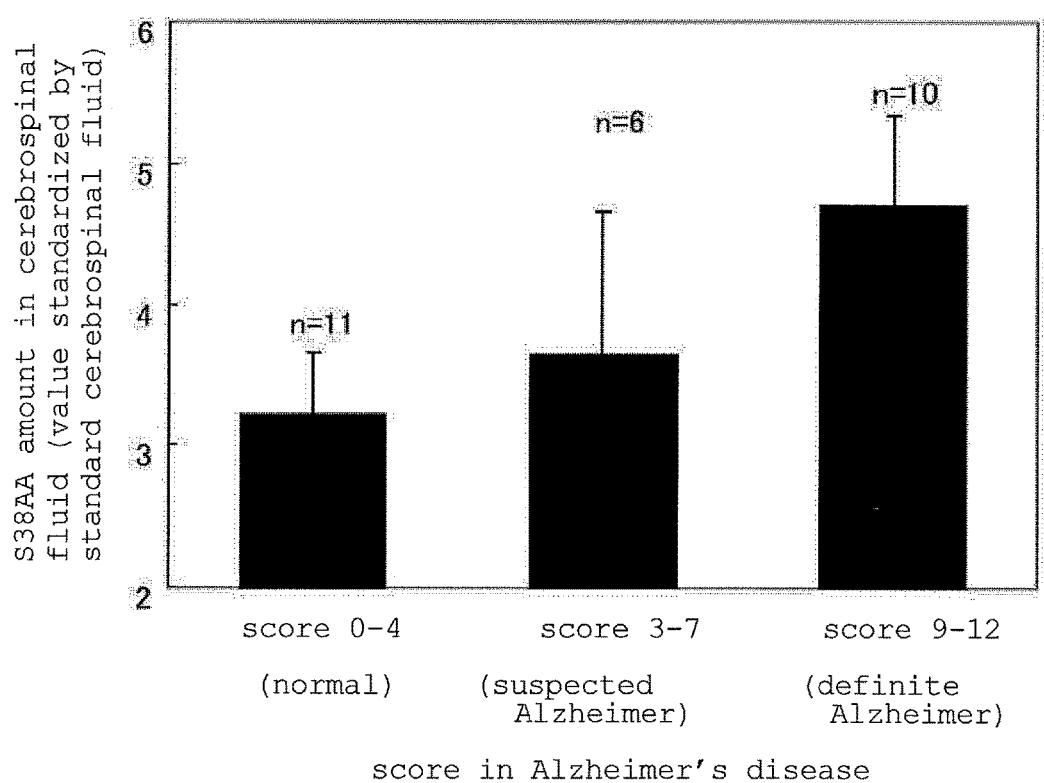
FIG. 5 shows the quantification results of S38AA fragments in the cerebrospinal fluid of non-Alzheimer's disease patients, patients with suspected Alzheimer's disease and patients with definite Alzheimer's disease, by Western blot method. The Y-axis shows the signal intensity of each group, which is standardized by the standard cerebrospinal fluid.

As shown in FIG. 5, it is clear that the amount of the S38AA fragment in the cerebrospinal fluid increases in Alzheimer's disease, and the amount of the S38AA fragment tends to increase even in patients with suspected Alzheimer's disease. This shows that the S38AA fragment increases from the early or preclinical stages of Alzheimer's disease, and a clear increase is observed in patients with definite Alzheimer's disease.

Figure 6:
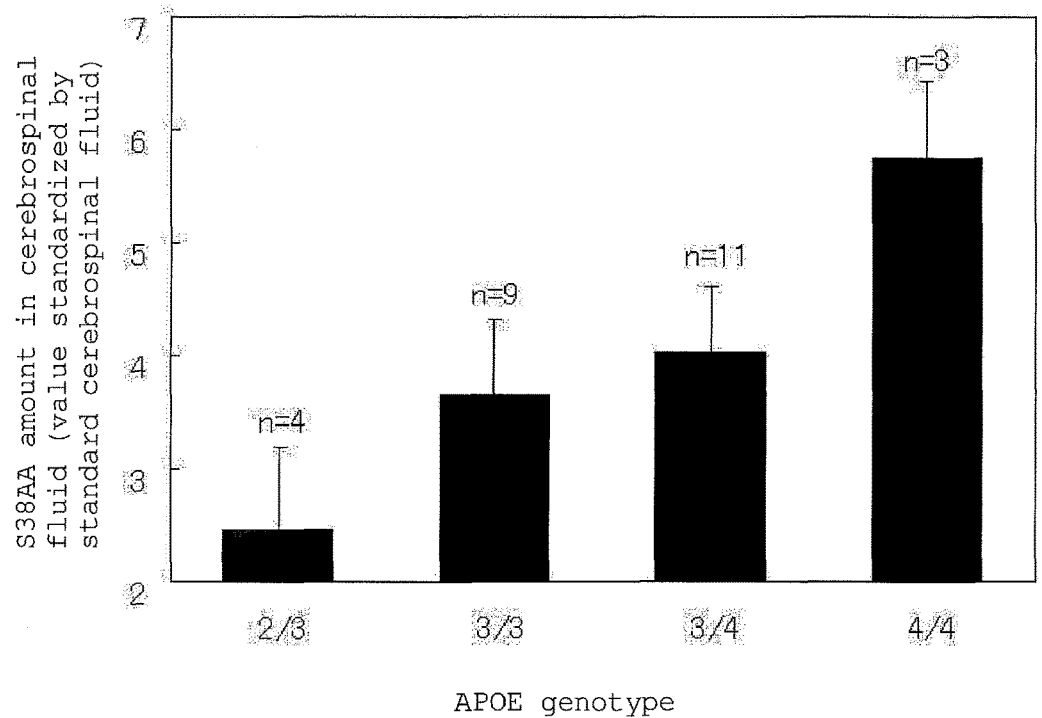
FIG. 6 shows the amount of an S38AA fragment in the cerebrospinal fluid of respective groups of all patients divided according to the APOE genotype (divided into 4 kinds of genotypes of ApoE2/3, ApoE3/3, ApoE3/4, ApoE4/4).

The whole patients were classified by APOE genotype (4 kinds of ApoE2/3, ApoE3/3, ApoE3/4, ApoE4/4; see Table 2), and the amount of S38AA in the cerebrospinal fluid of each group is shown in a graph (FIG. 6). The amount of the S38AA fragment remarkably increased particularly in the homozygous patients (ApoE4/4) having ApoE4. ApoE4 is an onset risk gene of Alzheimer's disease, and ApoE2 is considered to be a resistance factor of the onset of Alzheimer's disease. That is, FIG. 6 shows that the onset risk factors of Alzheimer's disease of APOE genotype and the amount of the S38AA fragment in the cerebrospinal fluid are correlated.

Figure 7:
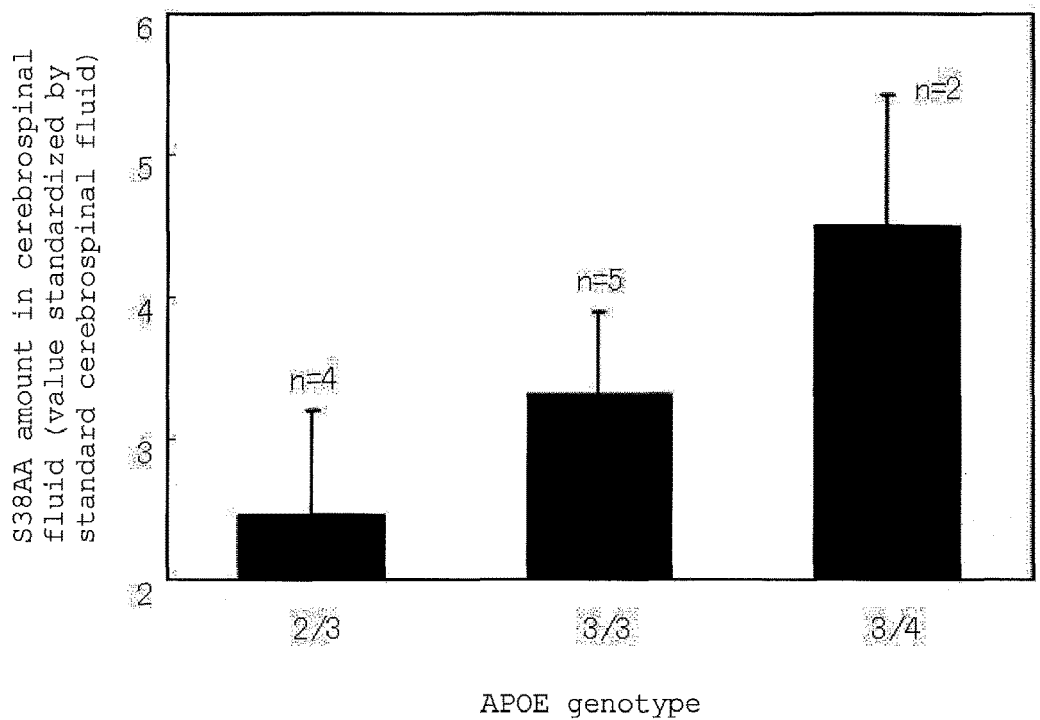
FIG. 7 shows the relationship between the amount of S38AA fragment and APOE genotype of 11 patients with non-Alzheimer's disease. The Y-axis shows the signal intensity of each group, which is standardized by the standard cerebrospinal fluid.

As for the relationship between the amount of the S38AA fragment in 11 non-Alzheimer's disease patients and the APOE genotype, the amount of the S38AA fragment in the cerebrospinal fluid increased in the order of ApoE2/3, ApoE3/3 and ApoE3/4, as shown in FIG. 7.

These correlations indicate that S38AA in the cerebrospinal fluid is correlated with the risk of the onset of Alzheimer's disease in the future, and further suggests that S38AA has a possibility of becoming a biomarker for estimating the risk of the onset of Alzheimer's disease in the future even in patients with preclinical Alzheimer's disease. Although early detection and the start of an early treatment are considered to be important in Alzheimer's disease, a diagnostic marker capable of early detection of Alzheimer's disease has not been found. Therefore, detection of the suspected Alzheimer's disease is extremely useful.

Example 3

Confirmation that S38AA Fragment in Cerebrospinal Fluid Contains S38AA Extra-membrane Region (1) Confirmation of S38AA Fragment Based on Antibody Used for Immunoprecipitation An anti-S38AA antibody (HPA023161 or HPA021374, Atlas Antibodies, 2 μL) for immunoprecipitation was added to the cerebrospinal fluid (500 μL) derived from patient with Alzheimer's disease and the mixture was incubated for 20 hr at 4° C., and thereafter incubated together with ProteinG Mag Sepharose (GE healthcare) for 1 hr at 4° C., whereby an S38AA fragment was immunoprecipitated. Thereafter, LDS sample buffer (Invitrogen, 10 μL) was added to magnetic beads to give a sample for SDS-PAGE (ProteinG Mag Sepharose bound fraction). In addition, 9 μL of the supernatant fraction free of precipitation by ProteinG Mag Sepharose was taken, and the LDS sample buffer (3 μL) was added to give a sample of an unbound fraction (ProteinG Mag Sepharose unbound fraction).

After performing SDS-PAGE in the same manner as in Example 1, Western blot was performed using HPA024631 as a primary antibody.

Figure 8:
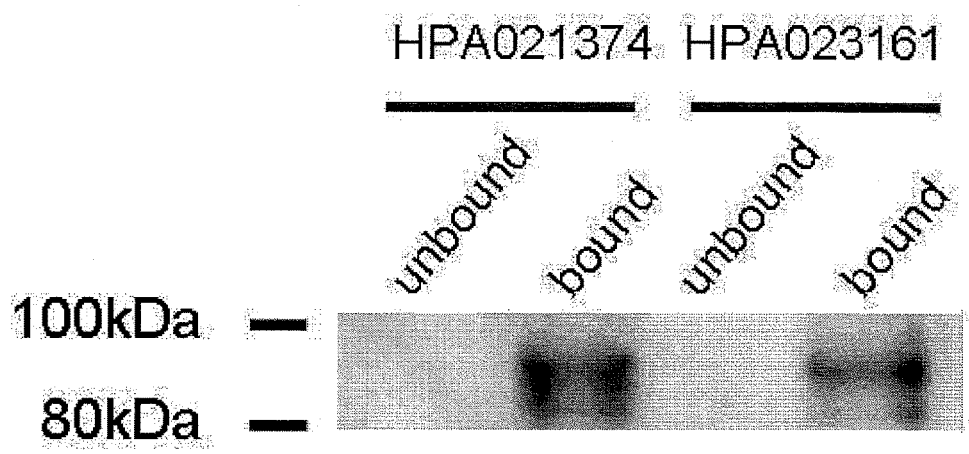
FIG. 8 shows the results of the molecular weight analysis of S38AA fragment specifically separated by an immunoprecipitation method using an anti-S38AA antibody (HPA021374, HPA023161).

As a result, in both HPA023161 and HPA021374 used for immunoprecipitation, an immunoprecipitate having a molecular weight similar to that found in the cerebrospinal fluid could be detected by Western blot (FIG. 8: bound lane). On the other hand, S38AA fragment was not detected in the supernatant of the immunoprecipitate (FIG. 8: unbound lane).

Since the amino acid sequences of the peptides used for producing the antibodies of HPA023161 and HPA021374 are MKPKQVSRDLGLAADLPGGAEGAAAQPQAVL-RQPE LRVISDGEQGGQQGHRLDHGGHLEMRKA (SEQ ID NO: 4; corresponding to the 926-988th amino acid region in SEQ ID NO: 2) and PVPHDKVVVDEGQ-DREVPEENKPPSRH AGGKAPGVQGQMAPPLPDSER-EKQEPEQGEVGKRPGQAQALEEAGDLPEDPQKVPE ADGQPA (SEQ ID NO: 5; corresponding to the 500-588th amino acid region in SEQ ID NO: 2), respectively, it has been shown that at least the S38AA fragment in the cerebrospinal fluid contains an amino acid sequence which is a part of these S38AA extra-membranous domain sequences.

(2) Confirmation of S38AA Fragment by Shotgun MS Analysis

To show that the immunoprecipitation sample of Example 3(1) contains the S38AA extra-membranous domain, MilliQ water (90 μL), 1 M Tris buffer (pH 8, 5 μL), urea (48 mg) and 0.5 M dithiothreitol (1 μL) were added to the two kinds of immunoprecipitation samples, and the mixtures were incubated at 30° C. for 2 hr. Thereafter, 0.5 M iodoacetamide (2 μL) was added, and the mixture was treated at room temperature for 1 hr to alkylate the thiol residue. Thereafter, 50 mM ammonium carbonate (750 μL) was added, trypsin (Promega, 2 μg) was added, and the mixture was incubated at 37° C. overnight to give a tryptic digest. The obtained tryptic digest was treated with trifluoroacetic acid to decrease the pH to 1-2, and purified by TopTip200 column (Glygen Corp.) according to the operation manual.

The tryptic digest immunoprecipitated by HPA023161 or HPA021374 was dissolved in 0.1% trifluoroacetic acid solution (20 μL), and 5 μL thereof was injected into an analysis column (Zorbax 300SB, 0.1×150 mm, Agilent Technologies). For the mobile phase of the analysis, 0.1% formic acid (mobile phase A) and 0.1% formic acid-methanol (mobile phase B) were used. A gradient program of increasing the concentration of mobile phase B linearly from 5% to 75% over 30 min, and thereafter to 98% mobile phase B (31 min), and maintaining for 5 min (36 min) was used. The mass spectrometer used was Thermo Fisher, LTQ velos system. The mass measurement range was set to 400-1400 m/z. Using the obtained data, peptide was identified using Mascot software version 2.2 and Swiss-Prot database (20110804).

The analysis parameter conditions on Mascot software are as follows.

monoisotopic mass was selected peptide mass tolerance: 15 Da fragment ion MS/MS tolerance: 0.8 Da digestive enzyme: trypsin was specified missed cleavage number: 1 at maximum methionine oxidation: allowed As a result of the shotgun MS analysis of the immunoprecipitates by HPA023161 and HPA021374, a total of 6 peptide sequences derived from the S38AA extra-membranous domain could be identified (FIG. 3, underlined part, SEQ ID NOs: 6-11). Therefore, it has been shown that the immunoprecipitates certainly contain the S38AA extra-membranous domain.

Example 4

Detection and Molecular Weight Prediction of S38AA Fragment in Plasma

Whether or not the S38AA fragment can be detected also in human plasma was studied. Heparin plasma was separated from patients with Alzheimer's disease and non-Alzheimer's disease patients. PureProteome albumin removal magnetic beads (Millipore, 500 μL) and ProteinG Mag Sepharose (GE healthcare, 60 μL) were placed in an Eppendorf tube, and washed with phosphate buffered saline. Thereafter, plasma (20 μL) and phosphate buffered saline (60 μL) were added to the mixed magnetic beads, and the mixture was incubated at 4° C. for 2 hr. The obtained plasma was confirmed by SDS-PAGE to be free of albumin and immunoglobulin. To this sample (60 μL) was added LDS sample buffer (Invitrogen, 20 μL) to give a sample for SDS-PAGE, which was analyzed by Western blot using HPA024631 as a primary antibody in the same manner as in the above-mentioned Example 3.

Figure 9:
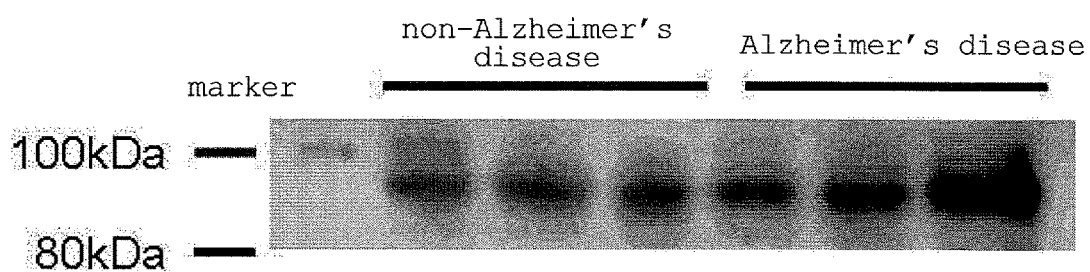
FIG. 9 shows an example of Western blot analysis of S38AA fragment in human plasma and the results of molecular weight analysis of the determined S38AA fragment.

As a result, a band considered to have the same molecular weight as that of the cerebrospinal fluid was found as shown in FIG. 9, and the amount of the corresponding band increased in patients with Alzheimer's disease.

Therefore, the S38AA fragment is also present in human plasma, and the amount of the S38AA fragment in plasma was clarified to increase in patients with Alzheimer's disease as compared to normal person.

Example 5

Detection Example 1 of S38AA Fragment Produced in Supernatant of Cultured Cell

BE(2)-C cell, SK-N-MC cell, SHSY-5Y cell and SHSY-5Y (APP) cell (cell line obtained by introducing human APP gene into SHSY-5Y cell) were cultured in D-MEM (Invitrogen) containing 10% fetal bovine serum for 2 days, and thereafter, the medium was recovered. Rat fetal primary nerve cell was cultured in Neurobasal medium (Invitrogen) containing B27 for 7 days, and the medium was recovered. HPA021374 antibody was added to each recovered medium (1 mL), and the mixture was incubated at 4° C. for 20 hr. Thereafter, ProteinG Mag Sepharose (30 μL) was added and the mixture was incubated at 4° C. for 2 hr. The magnetic beads were washed with PBS(−), and 4-fold diluted LDS sample buffer (20 μL) was added to give a sample for SDS-PAGE. In the same manner as in the above-mentioned Example 3, the sample was analyzed by Western blot using HPA024631 as a primary antibody.

As a result, a band considered to have the same molecular weight as that of the cerebrospinal fluid and plasma was observed. Therefore, it has been clarified that the cleavage of S38AA, namely, production and secretion of S38AA fragment, can be detected also in cultured cells and rat primary cultured cells, similar to human nerve cell.

Example 6

Detection Example 2 of S38AA Fragment Produced in Supernatant of Cultured Cell

An expression vector containing a DNA sequence added with Flag-Tag (DYKDDDDK; SEQ ID NO: 12) to the C-terminal of S38AA was constructed, and introduced into SHSY-5Y cell. After 48 hr, the medium (75 μL) was recovered, and LDS sample buffer (25 μL) was added to give a sample for SDS-PAGE. This time, the sample was analyzed by Western blot using an anti-Flag M2 monoclonal antibody (Sigma-Aldrich Corp.) as a primary antibody.

As a result, a band considered having the same molecular weight as that of the cerebrospinal fluid and plasma could be detected without immunoprecipitation, unlike Example 5. Therefore, it has been clarified that the gene introduction enables easier detection of S38AA fragment even in the culture supernatant of cultured cells.

INDUSTRIAL APPLICABILITY

According to the present invention, a determination agent and a determination method of Alzheimer's disease, which can determine not only patients affected with Alzheimer's disease but also patients having a high risk of developing Alzheimer's disease in the future, can be provided.

Furthermore, according to the present invention, a method of screening for a substance that treats or prevents Alzheimer's disease can be provided.

This application is based on a patent application No. 2010-293891 filed in Japan (filing date: Dec. 28, 2010), the contents of which are incorporated in full herein.

The invention claimed is:

1. A method of treating a test person affected with Alzheimer's disease or having a high possibility of being affected with Alzheimer's disease in the near future comprising the steps of:
   (1) detecting an S38AA fragment with an anti-S38AA antibody in a sample collected from the test person,
   (2) comparing the amount of S38AA fragment in the sample collected from the test person with an amount of S38AA fragment in a sample collected from a normal person,
   (3) determining the test person is affected with Alzheimer's disease or has a high possibility of being affected with Alzheimer's disease in the near future when the amount of S38AA fragment in the sample from the test person is high relative to the amount of S38AA fragment in the sample from the normal person, and
   (4) administering an agent capable of treating or preventing Alzheimer's disease to the test person who is determined to be affected with Alzheimer's disease or has a high possibility of being affected with Alzheimer's disease in the near future in step (3),
   wherein the S38AA is a polypeptide comprising the amino acid sequence shown by SEQ ID NO: 2,
   wherein the S38AA fragment is a polypeptide consisting of the S38AA extra-membranous domain or a partial polypeptide thereof,
   wherein the antibody is an antibody specifically recognizing an amino acid region selected from the following (a) to (c): (a) the 689-1119th amino acids of the amino acid sequence shown by SEQ ID NO: 2, (b) the 399-688th amino acids of the amino acid sequence shown by SEQ ID NO: 2, and (c) an amino acid region spanning both regions (a) and (b), and
   wherein the sample collected from the test person and the sample collected from the normal person are blood.

2. A method of starting an early treatment for suppressing the pathological progression by a symptomatic drug therapy for a test person affected with Alzheimer's disease or having a high possibility of being affected with Alzheimer's disease in the near future comprising the steps of:
   (1) detecting an S38AA fragment with an anti-S38AA antibody in a sample collected from the test person, (2) comparing the amount of S38AA fragment in the sample collected from the test person with an amount of S38AA fragment in a sample collected from a normal person,
(3) determining the test person is affected with Alzheimer's disease or has a high possibility of being affected with Alzheimer's disease in the near future when the amount of S38AA fragment in the sample from the test person is high relative to the amount of S38AA fragment in the sample from the normal person, and
(4) administering the symptomatic drug to the test person who is determined to be affected with Alzheimer's disease or has a high possibility of being affected with Alzheimer's disease in the near future in step (3),
wherein the S38AA is a polypeptide comprising the amino acid sequence shown by SEQ ID NO: 2,
wherein the S38AA fragment is a polypeptide consisting of the S38AA extra-membranous domain or a partial polypeptide thereof,
wherein the antibody is an antibody specifically recognizing an amino acid region selected from the following (a) to (c): (a) the 689-1119th amino acids of the amino acid sequence shown by SEQ ID NO: 2, (b) the 399-688th amino acids of the amino acid sequence shown by SEQ ID NO: 2, and (c) an amino acid region spanning both regions (a) and (b), and
wherein the sample collected from the test person and the sample collected from the normal person are blood.

* * * * *

SEQUENCE LISTING

<160> NUMBER OF SEQ ID NOS: 12

<210> SEQ ID NO 1
<211> LENGTH: 4303
<212> TYPE: DNA
<213> ORGANISM: Homo sapiens
<220> FEATURE:
<221> NAME/KEY: CDS
<222> LOCATION: (376)..(3735)

<400> SEQUENCE: 1

| | |
|---|---|
| cgccgcggcg gcagctgagt tgggctgagg tgtccctagc tggctctgcg gctcttccgg | 60 |
| gtctgggctc ggagattcac aggcggcccg cgaggccgag cgagggacgc atggccctga | 120 |
| ggcggccgca gggcttggcg gggtccggag gttgacctcg ccccgcagc cggccttcga | 180 |
| ggctgcctcc tccaggcagc tctgggggcc cgcgcccgcg cctgctcagg ctcccgtgtt | 240 |
| caggctgccc atccctccc caccggcgtc ccggacgttg ggacctgtga ccgtggcctc | 300 |
| gggctgggct tccaaagccg gccgcagccc ggcgaccccc gaggcctctc gccccgggcc | 360 |

| cctagacctc tcact | atg acc gcg gcc gcc gcc tcc aac tgg ggg ctg atc | 411 |
| | Met Thr Ala Ala Ala Ala Ser Asn Trp Gly Leu Ile | |
| | 1               5                   10           | |

| acg aac atc gtg aac agc atc gta ggg gtc agt gtc ctc acc atg ccc | 459 |
| Thr Asn Ile Val Asn Ser Ile Val Gly Val Ser Val Leu Thr Met Pro | |
|         15                  20                  25              | |

| ttc tgc ttc aaa cag tgc ggc atc gtc ctg ggg gcg ctg ctc ttg gtc | 507 |
| Phe Cys Phe Lys Gln Cys Gly Ile Val Leu Gly Ala Leu Leu Leu Val | |
|     30                  35                  40                  | |

| ttc tgc tca tgg atg acg cac cag tcg tgc atg ttc ttg gtg aag tcg | 555 |
| Phe Cys Ser Trp Met Thr His Gln Ser Cys Met Phe Leu Val Lys Ser | |
| 45                  50                  55                  60  | |

| gcc agc ctg agc aag cgg agg acc tac gcc ggc ctg gca ttc cac gcc | 603 |
| Ala Ser Leu Ser Lys Arg Arg Thr Tyr Ala Gly Leu Ala Phe His Ala | |
|                 65                  70                  75      | |

| tac ggg aag gca ggc aag atg ctg gtg gag acc agc atg atc ggg ctg | 651 |
| Tyr Gly Lys Ala Gly Lys Met Leu Val Glu Thr Ser Met Ile Gly Leu | |
|         80                  85                  90              | |

| atg ctg ggc acc tgc atc gcc ttc tac gtc gtg atc ggc gac ttg ggg | 699 |
| Met Leu Gly Thr Cys Ile Ala Phe Tyr Val Val Ile Gly Asp Leu Gly | |
|     95                  100                 105                 | |

| tcc aac ttc ttt gcc cgg ctg ttc ggg ttt cag gtg ggc ggc acc ttc | 747 |
| Ser Asn Phe Phe Ala Arg Leu Phe Gly Phe Gln Val Gly Gly Thr Phe | |
|         110                 115                 120             | |

| cgc atg ttc ctg ctg ttc gcc gtg tcg ctg tgc atc gtg ctc ccg ctc | 795 |
| Arg Met Phe Leu Leu Phe Ala Val Ser Leu Cys Ile Val Leu Pro Leu | |
| 125                 130                 135                 140 | |

| agc ctg cag cgg aac atg atg gcc tcc atc cag tcc ttc agc gcc atg | 843 |
| Ser Leu Gln Arg Asn Met Met Ala Ser Ile Gln Ser Phe Ser Ala Met | |
|                 145                 150                 155     | |

| gcc ctc ctc ttc tac acc gtg ttc atg ttc gtg atc gtg ctc tcc tct | 891 |
| Ala Leu Leu Phe Tyr Thr Val Phe Met Phe Val Ile Val Leu Ser Ser | |
|         160                 165                 170             | |

| ctc aag cac ggc ctc ttc agt ggg cag tgg ctg cgg cgg gtc agc tac | 939 |
| Leu Lys His Gly Leu Phe Ser Gly Gln Trp Leu Arg Arg Val Ser Tyr | |
|     175                 180                 185                 | |

| gtc cgc tgg gag ggc gtc ttc cgc tgc atc ccc atc ttc ggc atg tcc | 987 |
| Val Arg Trp Glu Gly Val Phe Arg Cys Ile Pro Ile Phe Gly Met Ser | |
|         190                 195                 200             | |

| ttc gcc tgc cag tcc cag gtg ctg ccc acc tac gac agc ctg gat gag | 1035 |
| Phe Ala Cys Gln Ser Gln Val Leu Pro Thr Tyr Asp Ser Leu Asp Glu | |

| | | | | | | | | | | | | | | | | |
|---|---|---|---|---|---|---|---|---|---|---|---|---|---|---|---|---|
| | | 205 | | | | 210 | | | | 215 | | | | 220 | | |
| ccg | tca | gtg | aaa | acc | atg | agc | tcc | ata | ttt | gct | tcc | tcc | ctt | aat | gtg | 1083 |
| Pro | Ser | Val | Lys | Thr | Met | Ser | Ser | Ile | Phe | Ala | Ser | Ser | Leu | Asn | Val | |
| | | | | 225 | | | | | 230 | | | | | 235 | | |
| gtc | acc | acc | ttc | tac | gtc | atg | gtg | ggg | ttt | ttc | ggc | tac | gtc | agc | ttc | 1131 |
| Val | Thr | Thr | Phe | Tyr | Val | Met | Val | Gly | Phe | Phe | Gly | Tyr | Val | Ser | Phe | |
| | | | 240 | | | | | 245 | | | | | 250 | | | |
| acc | gag | gcc | acg | gcc | ggc | aac | gtg | ctc | atg | cac | ttt | ccc | tcc | aac | ctg | 1179 |
| Thr | Glu | Ala | Thr | Ala | Gly | Asn | Val | Leu | Met | His | Phe | Pro | Ser | Asn | Leu | |
| | | 255 | | | | | 260 | | | | | 265 | | | | |
| gtg | acg | gag | atg | ctc | cgt | gtg | ggc | ttc | atg | atg | tca | gtg | gct | gtg | ggc | 1227 |
| Val | Thr | Glu | Met | Leu | Arg | Val | Gly | Phe | Met | Met | Ser | Val | Ala | Val | Gly | |
| 270 | | | | | 275 | | | | | 280 | | | | | | |
| ttc | ccc | atg | atg | atc | ctg | cca | tgc | agg | cag | gcc | ctg | agc | acg | ctg | ctg | 1275 |
| Phe | Pro | Met | Met | Ile | Leu | Pro | Cys | Arg | Gln | Ala | Leu | Ser | Thr | Leu | Leu | |
| 285 | | | | | 290 | | | | | 295 | | | | | 300 | |
| tgt | gag | cag | cag | caa | aaa | gat | ggc | acc | ttt | gca | gca | ggg | ggc | tac | atg | 1323 |
| Cys | Glu | Gln | Gln | Gln | Lys | Asp | Gly | Thr | Phe | Ala | Ala | Gly | Gly | Tyr | Met | |
| | | | | | 305 | | | | | 310 | | | | | 315 | |
| ccc | cct | ctc | cgg | ttt | aaa | gca | ctt | acc | ctc | tct | gtg | gtg | ttt | gga | acc | 1371 |
| Pro | Pro | Leu | Arg | Phe | Lys | Ala | Leu | Thr | Leu | Ser | Val | Val | Phe | Gly | Thr | |
| | | | 320 | | | | | 325 | | | | | 330 | | | |
| atg | gtt | ggt | ggc | atc | ctt | atc | ccc | aac | gtg | gag | acc | atc | ctg | ggc | ctc | 1419 |
| Met | Val | Gly | Gly | Ile | Leu | Ile | Pro | Asn | Val | Glu | Thr | Ile | Leu | Gly | Leu | |
| | | 335 | | | | | 340 | | | | | 345 | | | | |
| aca | gga | gcg | acc | atg | gga | agc | ctc | atc | tgc | ttc | atc | tgc | ccg | gcg | ctg | 1467 |
| Thr | Gly | Ala | Thr | Met | Gly | Ser | Leu | Ile | Cys | Phe | Ile | Cys | Pro | Ala | Leu | |
| | 350 | | | | | 355 | | | | | 360 | | | | | |
| atc | tac | aag | aaa | atc | cac | aag | aac | gca | ctt | tcc | tcc | cag | gtg | gtg | ctg | 1515 |
| Ile | Tyr | Lys | Lys | Ile | His | Lys | Asn | Ala | Leu | Ser | Ser | Gln | Val | Val | Leu | |
| 365 | | | | | 370 | | | | | 375 | | | | | 380 | |
| tgg | gtc | ggc | ctg | ggc | gtc | ctg | gtg | gtg | agc | act | gtc | acc | aca | ctg | tct | 1563 |
| Trp | Val | Gly | Leu | Gly | Val | Leu | Val | Val | Ser | Thr | Val | Thr | Thr | Leu | Ser | |
| | | | | 385 | | | | | 390 | | | | | 395 | | |
| gtg | agc | gag | gag | gtc | ccc | gag | gac | ttg | gca | gag | gaa | gcc | cct | ggc | ggc | 1611 |
| Val | Ser | Glu | Glu | Val | Pro | Glu | Asp | Leu | Ala | Glu | Glu | Ala | Pro | Gly | Gly | |
| | | | 400 | | | | | 405 | | | | | 410 | | | |
| cgg | ctt | gga | gag | gcc | gag | ggt | ttg | atg | aag | gtg | gag | gca | gcg | cgg | ctc | 1659 |
| Arg | Leu | Gly | Glu | Ala | Glu | Gly | Leu | Met | Lys | Val | Glu | Ala | Ala | Arg | Leu | |
| | | 415 | | | | | 420 | | | | | 425 | | | | |
| tca | gcc | cag | gat | ccg | gtt | gtg | gcc | gtg | gct | gag | gat | ggc | cgg | gag | aag | 1707 |
| Ser | Ala | Gln | Asp | Pro | Val | Val | Ala | Val | Ala | Glu | Asp | Gly | Arg | Glu | Lys | |
| | 430 | | | | | 435 | | | | | 440 | | | | | |
| ccg | aag | ctg | ccg | aag | gag | aga | gag | gag | ctg | gag | cag | gcc | cag | atc | aag | 1755 |
| Pro | Lys | Leu | Pro | Lys | Glu | Arg | Glu | Glu | Leu | Glu | Gln | Ala | Gln | Ile | Lys | |
| 445 | | | | | 450 | | | | | 455 | | | | | 460 | |
| ggg | ccc | gtg | gat | gtg | cct | gga | cgg | gaa | gat | ggc | aag | gag | gca | ccg | gag | 1803 |
| Gly | Pro | Val | Asp | Val | Pro | Gly | Arg | Glu | Asp | Gly | Lys | Glu | Ala | Pro | Glu | |
| | | | | 465 | | | | | 470 | | | | | 475 | | |
| gag | gca | cag | ctc | gat | cgc | cct | ggg | caa | ggg | att | gct | gtg | cct | gtg | ggc | 1851 |
| Glu | Ala | Gln | Leu | Asp | Arg | Pro | Gly | Gln | Gly | Ile | Ala | Val | Pro | Val | Gly | |
| | | | 480 | | | | | 485 | | | | | 490 | | | |
| gag | gcc | cac | cgc | cac | gag | cct | cct | gtt | cct | cac | gac | aag | gtg | gtg | gta | 1899 |
| Glu | Ala | His | Arg | His | Glu | Pro | Pro | Val | Pro | His | Asp | Lys | Val | Val | Val | |
| | | 495 | | | | | 500 | | | | | 505 | | | | |
| gat | gaa | ggc | caa | gac | cga | gag | gtg | cca | gaa | gag | aac | aaa | cct | cca | tcc | 1947 |
| Asp | Glu | Gly | Gln | Asp | Arg | Glu | Val | Pro | Glu | Glu | Asn | Lys | Pro | Pro | Ser | |
| | 510 | | | | | 515 | | | | | 520 | | | | | |
| aga | cac | gcg | ggc | gga | aag | gct | cca | ggg | gtc | cag | ggc | cag | atg | gcg | ccg | 1995 |

```
Arg His Ala Gly Gly Lys Ala Pro Gly Val Gln Gly Gln Met Ala Pro
525                 530                 535                 540 cct ctg ccc gac tca gaa aga gag aaa caa gag ccg gag cag gga gag       2043
Pro Leu Pro Asp Ser Glu Arg Glu Lys Gln Glu Pro Glu Gln Gly Glu
            545                 550                 555 gtt ggg aag agg cct gga cag gcc cag gcc ttg gag gag gcg ggt gat       2091
Val Gly Lys Arg Pro Gly Gln Ala Gln Ala Leu Glu Glu Ala Gly Asp
        560                 565                 570 ctt cct gaa gat ccc cag aaa gtt cca gaa gca gat ggt cag cca gct       2139
Leu Pro Glu Asp Pro Gln Lys Val Pro Glu Ala Asp Gly Gln Pro Ala
    575                 580                 585 gtc cag cct gca aag gag gac ctg ggg cca gga gac agg ggc ctg cat       2187
Val Gln Pro Ala Lys Glu Asp Leu Gly Pro Gly Asp Arg Gly Leu His
590                 595                 600 cct cgg ccc cag gca gtg ctg tct gag cag cag aac ggc ctg gcg gtg       2235
Pro Arg Pro Gln Ala Val Leu Ser Glu Gln Gln Asn Gly Leu Ala Val
605                 610                 615                 620 ggt gga ggg gaa aag gcc aag ggg gga ccg ccg cca ggc aac gcc gcc       2283
Gly Gly Gly Glu Lys Ala Lys Gly Gly Pro Pro Pro Gly Asn Ala Ala
            625                 630                 635 ggg gac aca ggg cag ccc gca gag gac agc gac cac ggt ggg aag cct       2331
Gly Asp Thr Gly Gln Pro Ala Glu Asp Ser Asp His Gly Gly Lys Pro
        640                 645                 650 ccc ctc cca gcg gag aag ccg gct cca ggg cct ggg ctg ccg ccc gag       2379
Pro Leu Pro Ala Glu Lys Pro Ala Pro Gly Pro Gly Leu Pro Pro Glu
    655                 660                 665 cct cgc gag cag agg gac gtg gag cga gcg ggt gga aac cag gcg gcc       2427
Pro Arg Glu Gln Arg Asp Val Glu Arg Ala Gly Gly Asn Gln Ala Ala
670                 675                 680 agc cag ctg gag gaa gct ggc agg gcg gag atg ctg gac cac gcc gtc       2475
Ser Gln Leu Glu Glu Ala Gly Arg Ala Glu Met Leu Asp His Ala Val
685                 690                 695                 700 ctg ctt cag gtg atc aaa gaa cag cag gtg cag caa aag cgc ttg ctg       2523
Leu Leu Gln Val Ile Lys Glu Gln Gln Val Gln Gln Lys Arg Leu Leu
            705                 710                 715 gac cag cag gag aag ctg ctg gcg gtg atc gag gag cag cac aag gag       2571
Asp Gln Gln Glu Lys Leu Leu Ala Val Ile Glu Glu Gln His Lys Glu
        720                 725                 730 atc cac cag cag agg cag gag gac gag gag gat aaa ccc agg cag gtg       2619
Ile His Gln Gln Arg Gln Glu Asp Glu Glu Asp Lys Pro Arg Gln Val
    735                 740                 745 gag gtg cat caa gag ccc ggg gca gcg gtg ccc aga ggc cag gag gcc       2667
Glu Val His Gln Glu Pro Gly Ala Ala Val Pro Arg Gly Gln Glu Ala
750                 755                 760 cct gaa ggc aag gcc agg gag acg gtg gag aat ctg cct ccc ctg cct       2715
Pro Glu Gly Lys Ala Arg Glu Thr Val Glu Asn Leu Pro Pro Leu Pro
765                 770                 775                 780 ttg gac cct gtc ctc aga gct cct ggg ggc cgc cct gct cca tcc cag       2763
Leu Asp Pro Val Leu Arg Ala Pro Gly Gly Arg Pro Ala Pro Ser Gln
            785                 790                 795 gac ctt aac cag cgc tcc ctg gag cac tct gag ggg cct gtg ggc aga       2811
Asp Leu Asn Gln Arg Ser Leu Glu His Ser Glu Gly Pro Val Gly Arg
        800                 805                 810 gac cct gct ggc cct cct gac ggc ggc cct gac aca gag cct cgg gca       2859
Asp Pro Ala Gly Pro Pro Asp Gly Gly Pro Asp Thr Glu Pro Arg Ala
    815                 820                 825 gcc cag gcc aag ctg aga gat ggc cag aag gat gcc gcc ccc agg gca       2907
Ala Gln Ala Lys Leu Arg Asp Gly Gln Lys Asp Ala Ala Pro Arg Ala
830                 835                 840
```

```
gct ggc act gtg aag gag ctc ccc aag ggc ccg gag cag gtg ccc gtg    2955
Ala Gly Thr Val Lys Glu Leu Pro Lys Gly Pro Glu Gln Val Pro Val
845             850                 855                 860 cca gac ccc gcc agg gaa gcc ggg ggc cca gag gag cgc ctc gca gag    3003
Pro Asp Pro Ala Arg Glu Ala Gly Gly Pro Glu Glu Arg Leu Ala Glu
            865                 870                 875 gaa ttc cct ggg caa agt cag gac gtt act ggc ggt tcc caa gac agg    3051
Glu Phe Pro Gly Gln Ser Gln Asp Val Thr Gly Gly Ser Gln Asp Arg
        880                 885                 890 aaa aaa cct ggg aag gag gtg gca gcc act ggc acc agc att ctg aag    3099
Lys Lys Pro Gly Lys Glu Val Ala Ala Thr Gly Thr Ser Ile Leu Lys
    895                 900                 905 gaa gcc aac tgg ctc gtg gca ggg cca gga gca gag acg ggg gac cct    3147
Glu Ala Asn Trp Leu Val Ala Gly Pro Gly Ala Glu Thr Gly Asp Pro
910                 915                 920 cgc atg aag ccc aag caa gtg agc cga gac ctg ggc ctt gca gcg gac    3195
Arg Met Lys Pro Lys Gln Val Ser Arg Asp Leu Gly Leu Ala Ala Asp
925             930                 935                 940 ctg ccc ggt ggg gcg gaa gga gca gct gca cag ccc cag gct gtg tta    3243
Leu Pro Gly Gly Ala Glu Gly Ala Ala Ala Gln Pro Gln Ala Val Leu
            945                 950                 955 cgc cag ccg gaa ctg cgg gtc atc tct gat ggc gag cag ggt gga cag    3291
Arg Gln Pro Glu Leu Arg Val Ile Ser Asp Gly Glu Gln Gly Gly Gln
        960                 965                 970 cag ggc cac cgg ctg gac cat ggc ggt cac ctg gag atg aga aag gcc    3339
Gln Gly His Arg Leu Asp His Gly Gly His Leu Glu Met Arg Lys Ala
    975                 980                 985 cgc ggg ggg gac cat gtg cct gtg tcc cac gag cag ccg aga ggc ggg    3387
Arg Gly Gly Asp His Val Pro Val Ser His Glu Gln Pro Arg Gly Gly
990                 995                 1000 gag  gac gct gct gtc cag  gag ccc agg cag agg  cca gag cca gag    3432
Glu  Asp Ala Ala Val Gln  Glu Pro Arg Gln Arg  Pro Glu Pro Glu
1005              1010                 1015 ctg  ggg ctc aaa cga gct  gtc ccg ggg ggc cag  agg ccg gac aat    3477
Leu  Gly Leu Lys Arg Ala  Val Pro Gly Gly Gln  Arg Pro Asp Asn
1020              1025                 1030 gcc  aag ccc aac cgg gac  ctg aaa ctg cag gct  ggc tcc gac ctc    3522
Ala  Lys Pro Asn Arg Asp  Leu Lys Leu Gln Ala  Gly Ser Asp Leu
1035              1040                 1045 cgg  agg cga cgg cgg gac  ctt ggc cct cat gca  gag ggt cag ctg    3567
Arg  Arg Arg Arg Arg Asp  Leu Gly Pro His Ala  Glu Gly Gln Leu
1050              1055                 1060 gcc  ccg agg gat ggg gtc  atc att ggc ctt aac  ccc ctg cct gat    3612
Ala  Pro Arg Asp Gly Val  Ile Ile Gly Leu Asn  Pro Leu Pro Asp
1065              1070                 1075 gtc  cag gtg aac gac ctc  cgt ggc gcc ctg gat  gcc cag ctc cgc    3657
Val  Gln Val Asn Asp Leu  Arg Gly Ala Leu Asp  Ala Gln Leu Arg
1080              1085                 1090 cag  gct gcg ggg gga gct  ctg cag gtg gtc cac  agc cgg cag ctt    3702
Gln  Ala Ala Gly Gly Ala  Leu Gln Val Val His  Ser Arg Gln Leu
1095              1100                 1105 aga  cag gcg cct ggg cct  cca gag gag tcc tag cacctgctgg           3745
Arg  Gln Ala Pro Gly Pro  Pro Glu Glu Ser
1110              1115 ccatgagggc cacgccagcc actgccctcc tcggccagca gcaggtctgt ctcagccgca   3805
tcccagccaa actctggagg tcacactcgc ctctccccag ggtttcatgt ctgaggccct   3865
caccaagtgt gagtgacagt ataaaagatt cactgtggca tcgttccag aatgttcttg    3925 ctgtcgttct gttgcagctc ttagtctgag gtcctctgac ctctagactc tgagctcact   3985
```

-continued

```
ccagcctgtg aggagaaacg gcctccgctg cgagctggct ggtgcactcc caggctcagg    4045
ctggggagct gctgcgtctg tggtcaggcc tcctgctcct gccagggagc acgcgtggtc    4105
ttcgggttga gctcggccgt gcgtggaggt gcgcatggct gctcatggtc ccaacacagg    4165
ctactgtgag agccagcatc caaccccacg cttgcagtga ctcagaatga taattattat    4225
gactgtttat cgatgcttcc cacagtgtgg tagaaagtct tgaataaaca cttttgcctt    4285
cacccagaaa aaaaaaaa                                                  4303
```

<210> SEQ ID NO 2
<211> LENGTH: 1119
<212> TYPE: PRT
<213> ORGANISM: Homo sapiens

<400> SEQUENCE: 2

```
Met Thr Ala Ala Ala Ser Asn Trp Gly Leu Ile Thr Asn Ile Val
 1               5                  10                  15

Asn Ser Ile Val Gly Val Ser Val Leu Thr Met Pro Phe Cys Phe Lys
                20                  25                  30

Gln Cys Gly Ile Val Leu Gly Ala Leu Leu Leu Val Phe Cys Ser Trp
            35                  40                  45

Met Thr His Gln Ser Cys Met Phe Leu Val Lys Ser Ala Ser Leu Ser
        50                  55                  60

Lys Arg Arg Thr Tyr Ala Gly Leu Ala Phe His Ala Tyr Gly Lys Ala
    65                  70                  75                  80

Gly Lys Met Leu Val Glu Thr Ser Met Ile Gly Leu Met Leu Gly Thr
                85                  90                  95

Cys Ile Ala Phe Tyr Val Val Ile Gly Asp Leu Gly Ser Asn Phe Phe
            100                 105                 110

Ala Arg Leu Phe Gly Phe Gln Val Gly Gly Thr Phe Arg Met Phe Leu
        115                 120                 125

Leu Phe Ala Val Ser Leu Cys Ile Val Leu Pro Leu Ser Leu Gln Arg
    130                 135                 140

Asn Met Met Ala Ser Ile Gln Ser Phe Ser Ala Met Ala Leu Leu Phe
145                 150                 155                 160

Tyr Thr Val Phe Met Phe Val Ile Val Leu Ser Ser Leu Lys His Gly
                165                 170                 175

Leu Phe Ser Gly Gln Trp Leu Arg Arg Val Ser Tyr Val Arg Trp Glu
            180                 185                 190

Gly Val Phe Arg Cys Ile Pro Ile Phe Gly Met Ser Phe Ala Cys Gln
        195                 200                 205

Ser Gln Val Leu Pro Thr Tyr Asp Ser Leu Asp Glu Pro Ser Val Lys
    210                 215                 220

Thr Met Ser Ser Ile Phe Ala Ser Ser Leu Asn Val Val Thr Thr Phe
225                 230                 235                 240

Tyr Val Met Val Gly Phe Phe Gly Tyr Val Ser Phe Thr Glu Ala Thr
                245                 250                 255

Ala Gly Asn Val Leu Met His Phe Pro Ser Asn Leu Val Thr Glu Met
            260                 265                 270

Leu Arg Val Gly Phe Met Met Ser Val Ala Val Gly Phe Pro Met Met
        275                 280                 285

Ile Leu Pro Cys Arg Gln Ala Leu Ser Thr Leu Leu Cys Glu Gln Gln
    290                 295                 300

Gln Lys Asp Gly Thr Phe Ala Ala Gly Gly Tyr Met Pro Pro Leu Arg
```

```
            305                 310                 315                 320
        Phe Lys Ala Leu Thr Leu Ser Val Val Phe Gly Thr Met Val Gly Gly
                        325                 330                 335
        Ile Leu Ile Pro Asn Val Glu Thr Ile Leu Gly Leu Thr Gly Ala Thr
                        340                 345                 350
        Met Gly Ser Leu Ile Cys Phe Ile Cys Pro Ala Leu Ile Tyr Lys Lys
                        355                 360                 365
        Ile His Lys Asn Ala Leu Ser Ser Gln Val Val Leu Trp Val Gly Leu
                        370                 375                 380
        Gly Val Leu Val Val Ser Thr Val Thr Thr Leu Ser Val Ser Glu Glu
        385                 390                 395                 400
        Val Pro Glu Asp Leu Ala Glu Ala Pro Gly Gly Arg Leu Gly Glu
        465                 405                 410                 415
        Ala Glu Gly Leu Met Lys Val Glu Ala Ala Arg Leu Ser Ala Gln Asp
                        420                 425                 430
        Pro Val Val Ala Val Ala Glu Asp Gly Arg Glu Lys Pro Lys Leu Pro
                        435                 440                 445
        Lys Glu Arg Glu Glu Leu Glu Gln Ala Gln Ile Lys Gly Pro Val Asp
                        450                 455                 460
        Val Pro Gly Arg Glu Asp Gly Lys Glu Ala Pro Glu Glu Ala Gln Leu
        465                 470                 475                 480
        Asp Arg Pro Gly Gln Gly Ile Ala Val Pro Val Gly Glu Ala His Arg
                        485                 490                 495
        His Glu Pro Pro Val Pro His Asp Lys Val Val Asp Glu Gly Gln
                        500                 505                 510
        Asp Arg Glu Val Pro Glu Glu Asn Lys Pro Pro Ser Arg His Ala Gly
                        515                 520                 525
        Gly Lys Ala Pro Gly Val Gln Gly Gln Met Ala Pro Pro Leu Pro Asp
                        530                 535                 540
        Ser Glu Arg Glu Lys Gln Glu Pro Glu Gln Gly Glu Val Gly Lys Arg
        545                 550                 555                 560
        Pro Gly Gln Ala Gln Ala Leu Glu Glu Ala Gly Asp Leu Pro Glu Asp
                        565                 570                 575
        Pro Gln Lys Val Pro Glu Ala Asp Gly Gln Pro Ala Val Gln Pro Ala
                        580                 585                 590
        Lys Glu Asp Leu Gly Pro Gly Asp Arg Gly Leu His Pro Arg Pro Gln
                        595                 600                 605
        Ala Val Leu Ser Glu Gln Gln Asn Gly Leu Ala Val Gly Gly Gly Glu
                        610                 615                 620
        Lys Ala Lys Gly Gly Pro Pro Gly Asn Ala Ala Gly Asp Thr Gly
        625                 630                 635                 640
        Gln Pro Ala Glu Asp Ser Asp His Gly Lys Pro Pro Leu Pro Ala
                        645                 650                 655
        Glu Lys Pro Ala Pro Gly Pro Gly Leu Pro Pro Glu Pro Arg Glu Gln
                        660                 665                 670
        Arg Asp Val Glu Arg Ala Gly Gly Asn Gln Ala Ala Ser Gln Leu Glu
                        675                 680                 685
        Glu Ala Gly Arg Ala Glu Met Leu Asp His Ala Val Leu Leu Gln Val
                        690                 695                 700
        Ile Lys Glu Gln Gln Val Gln Gln Lys Arg Leu Leu Asp Gln Gln Glu
        705                 710                 715                 720
        Lys Leu Leu Ala Val Ile Glu Glu Gln His Lys Glu Ile His Gln Gln
                        725                 730                 735
```

-continued

Arg Gln Glu Asp Glu Glu Asp Lys Pro Arg Gln Val Glu Val His Gln
            740                 745                 750

Glu Pro Gly Ala Ala Val Pro Arg Gly Gln Glu Ala Pro Glu Gly Lys
            755                 760                 765

Ala Arg Glu Thr Val Glu Asn Leu Pro Pro Leu Pro Leu Asp Pro Val
            770                 775                 780

Leu Arg Ala Pro Gly Gly Arg Pro Ala Pro Ser Gln Asp Leu Asn Gln
785                 790                 795                 800

Arg Ser Leu Glu His Ser Glu Pro Val Gly Arg Asp Pro Ala Gly
            805                 810                 815

Pro Pro Asp Gly Gly Pro Asp Thr Glu Pro Arg Ala Ala Gln Ala Lys
            820                 825                 830

Leu Arg Asp Gly Gln Lys Asp Ala Ala Pro Arg Ala Ala Gly Thr Val
            835                 840                 845

Lys Glu Leu Pro Lys Gly Pro Glu Gln Val Pro Val Pro Asp Pro Ala
            850                 855                 860

Arg Glu Ala Gly Gly Pro Glu Glu Arg Leu Ala Glu Glu Phe Pro Gly
865                 870                 875                 880

Gln Ser Gln Asp Val Thr Gly Gly Ser Gln Asp Arg Lys Lys Pro Gly
            885                 890                 895

Lys Glu Val Ala Ala Thr Gly Thr Ser Ile Leu Lys Glu Ala Asn Trp
            900                 905                 910

Leu Val Ala Gly Pro Gly Ala Glu Thr Gly Asp Pro Arg Met Lys Pro
            915                 920                 925

Lys Gln Val Ser Arg Asp Leu Gly Leu Ala Ala Asp Leu Pro Gly Gly
            930                 935                 940

Ala Glu Gly Ala Ala Ala Gln Pro Gln Ala Val Leu Arg Gln Pro Glu
945                 950                 955                 960

Leu Arg Val Ile Ser Asp Gly Glu Gln Gly Gly Gln Gly His Arg
            965                 970                 975

Leu Asp His Gly Gly His Leu Glu Met Arg Lys Ala Arg Gly Gly Asp
            980                 985                 990

His Val Pro Val Ser His Glu Gln Pro Arg Gly Gly Glu Asp Ala Ala
            995                 1000                1005

Val Gln Glu Pro Arg Gln Arg Pro Glu Pro Glu Leu Gly Leu Lys
            1010                1015                1020

Arg Ala Val Pro Gly Gly Gln Arg Pro Asp Asn Ala Lys Pro Asn
            1025                1030                1035

Arg Asp Leu Lys Leu Gln Ala Gly Ser Asp Leu Arg Arg Arg Arg
            1040                1045                1050

Arg Asp Leu Gly Pro His Ala Glu Gly Gln Leu Ala Pro Arg Asp
            1055                1060                1065

Gly Val Ile Ile Gly Leu Asn Pro Leu Pro Asp Val Gln Val Asn
            1070                1075                1080

Asp Leu Arg Gly Ala Leu Asp Ala Gln Leu Arg Gln Ala Ala Gly
            1085                1090                1095

Gly Ala Leu Gln Val Val His Ser Arg Gln Leu Arg Gln Ala Pro
            1100                1105                1110

Gly Pro Pro Glu Glu Ser
            1115

<210> SEQ ID NO 3
<211> LENGTH: 10

```
<212> TYPE: PRT
<213> ORGANISM: Homo sapiens

<400> SEQUENCE: 3

Gly Gln Glu Ala Pro Glu Gly Lys Ala Arg
1               5                   10

<210> SEQ ID NO 4
<211> LENGTH: 63
<212> TYPE: PRT
<213> ORGANISM: Homo sapiens

<400> SEQUENCE: 4

Met Lys Pro Lys Gln Val Ser Arg Asp Leu Gly Leu Ala Ala Asp Leu
1               5                   10                  15

Pro Gly Gly Ala Glu Gly Ala Ala Gln Pro Gln Ala Val Leu Arg
            20                  25                  30

Gln Pro Glu Leu Arg Val Ile Ser Asp Gly Glu Gln Gly Gly Gln Gln
        35                  40                  45

Gly His Arg Leu Asp His Gly Gly His Leu Glu Met Arg Lys Ala
    50                  55                  60

<210> SEQ ID NO 5
<211> LENGTH: 89
<212> TYPE: PRT
<213> ORGANISM: Homo sapiens

<400> SEQUENCE: 5

Pro Val Pro His Asp Lys Val Val Asp Glu Gly Gln Asp Arg Glu
1               5                   10                  15

Val Pro Glu Glu Asn Lys Pro Pro Ser Arg His Ala Gly Gly Lys Ala
            20                  25                  30

Pro Gly Val Gln Gly Gln Met Ala Pro Pro Leu Pro Asp Ser Glu Arg
        35                  40                  45

Glu Lys Gln Glu Pro Glu Gln Gly Glu Val Gly Lys Arg Pro Gly Gln
    50                  55                  60

Ala Gln Ala Leu Glu Glu Ala Gly Asp Leu Pro Glu Asp Pro Gln Lys
65                  70                  75                  80

Val Pro Glu Ala Asp Gly Gln Pro Ala
                85

<210> SEQ ID NO 6
<211> LENGTH: 11
<212> TYPE: PRT
<213> ORGANISM: Homo sapiens

<400> SEQUENCE: 6

Lys Val Val Val Asp Glu Gly Gln Asp Arg Glu
1               5                   10

<210> SEQ ID NO 7
<211> LENGTH: 12
<212> TYPE: PRT
<213> ORGANISM: Homo sapiens

<400> SEQUENCE: 7

Lys Leu Leu Ala Val Ile Glu Glu Gln His Lys Glu
1               5                   10

<210> SEQ ID NO 8
<211> LENGTH: 13
```

```
<212> TYPE: PRT
<213> ORGANISM: Homo sapiens

<400> SEQUENCE: 8

Arg Ser Leu Glu His Ser Glu Gly Pro Val Gly Arg Asp
1               5                   10

<210> SEQ ID NO 9
<211> LENGTH: 16
<212> TYPE: PRT
<213> ORGANISM: Homo sapiens

<400> SEQUENCE: 9

Leu Pro Lys Gly Pro Glu Gln Val Pro Val Pro Asp Pro Ala Arg Glu
1               5                   10                  15

<210> SEQ ID NO 10
<211> LENGTH: 15
<212> TYPE: PRT
<213> ORGANISM: Homo sapiens

<400> SEQUENCE: 10

Arg Leu Asp His Gly Gly His Leu Glu Met Arg Lys Ala Arg Gly
1               5                   10                  15

<210> SEQ ID NO 11
<211> LENGTH: 13
<212> TYPE: PRT
<213> ORGANISM: Homo sapiens

<400> SEQUENCE: 11

Arg Gly Gly Glu Asp Ala Ala Val Gln Glu Pro Arg Gln
1               5                   10

<210> SEQ ID NO 12
<211> LENGTH: 8
<212> TYPE: PRT
<213> ORGANISM: Homo sapiens

<400> SEQUENCE: 12

Asp Tyr Lys Asp Asp Asp Asp Lys
1               5
```